(12) United States Patent
Matzinger

(10) Patent No.: US 6,558,528 B1
(45) Date of Patent: May 6, 2003

(54) ELECTROCHEMICAL TEST STRIP CARDS THAT INCLUDE AN INTEGRAL DESSICANT

(75) Inventor: David Parkes Matzinger, Menlo Park, CA (US)

(73) Assignee: Lifescan, Inc., Milpitas, CA (US)

( * ) Notice: Subject to any disclaimer, the term of this patent is extended or adjusted under 35 U.S.C. 154(b) by 123 days.

(21) Appl. No.: 09/746,116

(22) Filed: Dec. 20, 2000

(51) Int. Cl.[7] .............................................. G01N 27/327
(52) U.S. Cl. .............................. 205/777.5; 204/403.14; 205/792
(58) Field of Search ................... 204/403.01–403.15, 204/416–419; 205/777.5, 789, 775, 792; 422/82.01–82.03

(56) References Cited

U.S. PATENT DOCUMENTS

| | | | | |
|---|---|---|---|---|
| 5,437,999 A | * | 8/1995 | Diebold et al. | 204/403.11 |
| 5,708,247 A | | 1/1998 | McAleer et al. | 204/403.05 |
| 5,942,102 A | | 8/1999 | Hodges et al. | 205/775 |
| 5,951,836 A | | 9/1999 | McAleer et al. | 205/777.5 |
| 5,972,199 A | | 10/1999 | Heller et al. | 205/777.5 |
| 5,989,917 A | | 11/1999 | McAleer et al. | 436/46 |
| 5,997,817 A | | 12/1999 | Crismore et al. | 204/403.1 |
| 6,125,292 A | | 9/2000 | Uenoyama et al. | 435/14 |
| 6,151,110 A | | 11/2000 | Markart | 356/244 |

FOREIGN PATENT DOCUMENTS

| | | |
|---|---|---|
| EP | 0 871 033 A2 | 10/1998 |
| WO | WO 97/18465 | 5/1997 |
| WO | WO 97/27483 | 7/1997 |

\* cited by examiner

*Primary Examiner*—T. Tung
*Assistant Examiner*—Alex Noguerola
(74) *Attorney, Agent, or Firm*—Carol M. LaSalle; Bozicevic, Field & Francis, LLP

(57) ABSTRACT

Electrochemical test strip cards that can be singulated to produce electrochemical test strips are provided. The electrochemical test cards are made up of two or more electrochemical test strip precursors, where each precursor is characterized by the presence of a dry reagent housing reaction chamber bounded by opposing electrodes. In gaseous communication with each reaction chamber of the card is an integrated desiccant. Also provided are methods of using the subject electrochemical test strips cards, as well as kits that include the same. The subject test strips and cards find use in the detection/concentration determination of a number of different analytes, including glucose.

27 Claims, 18 Drawing Sheets

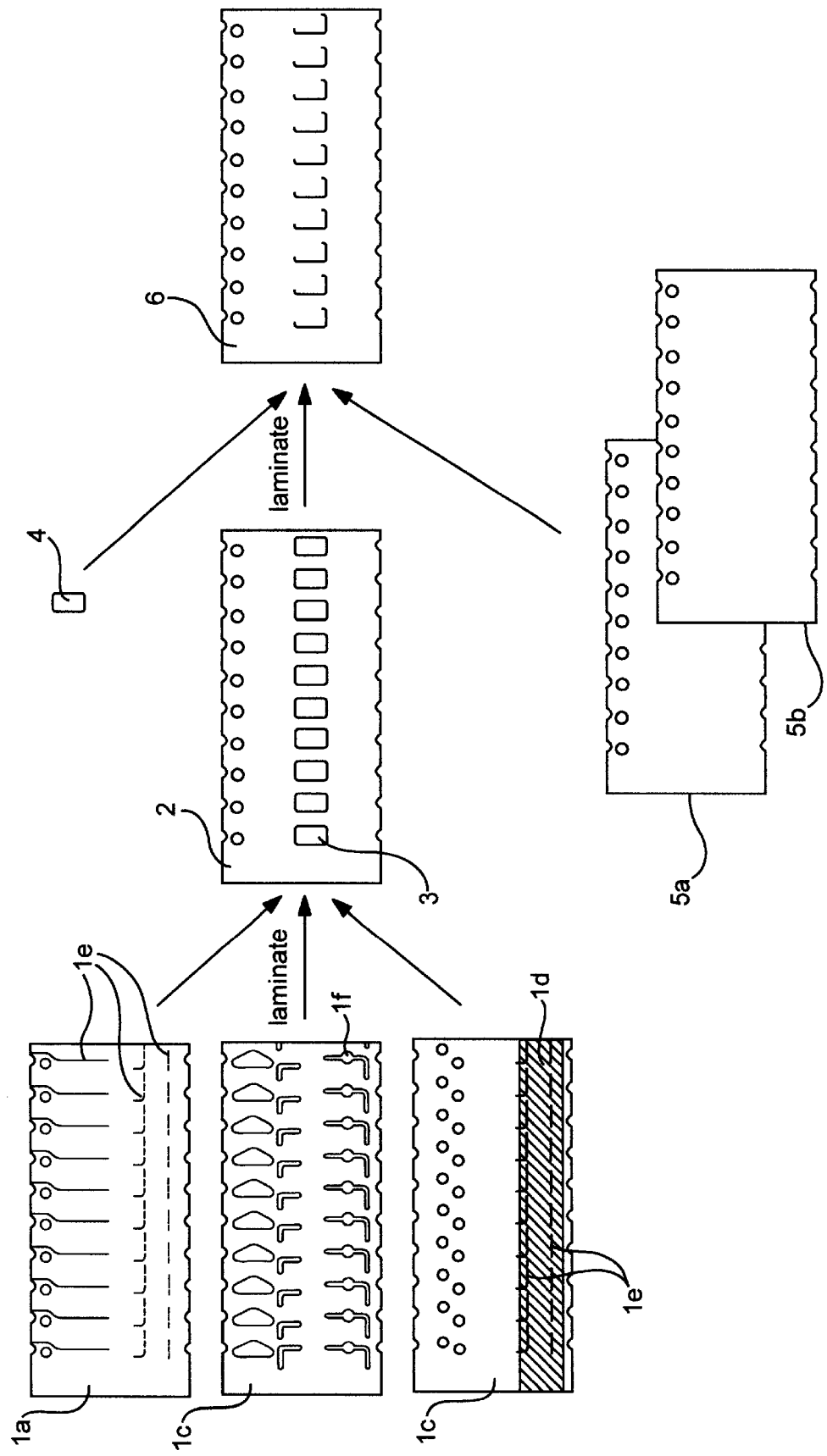

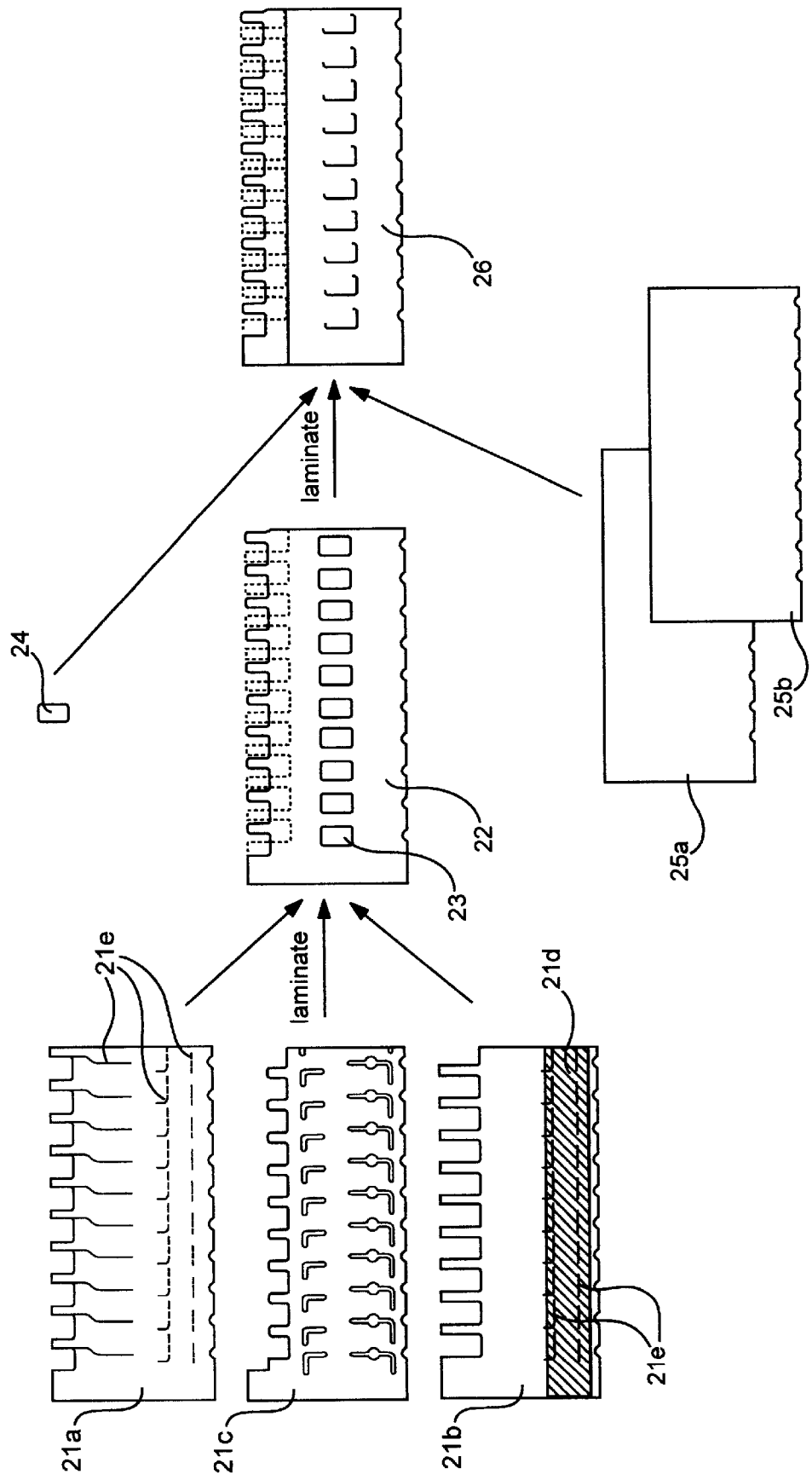

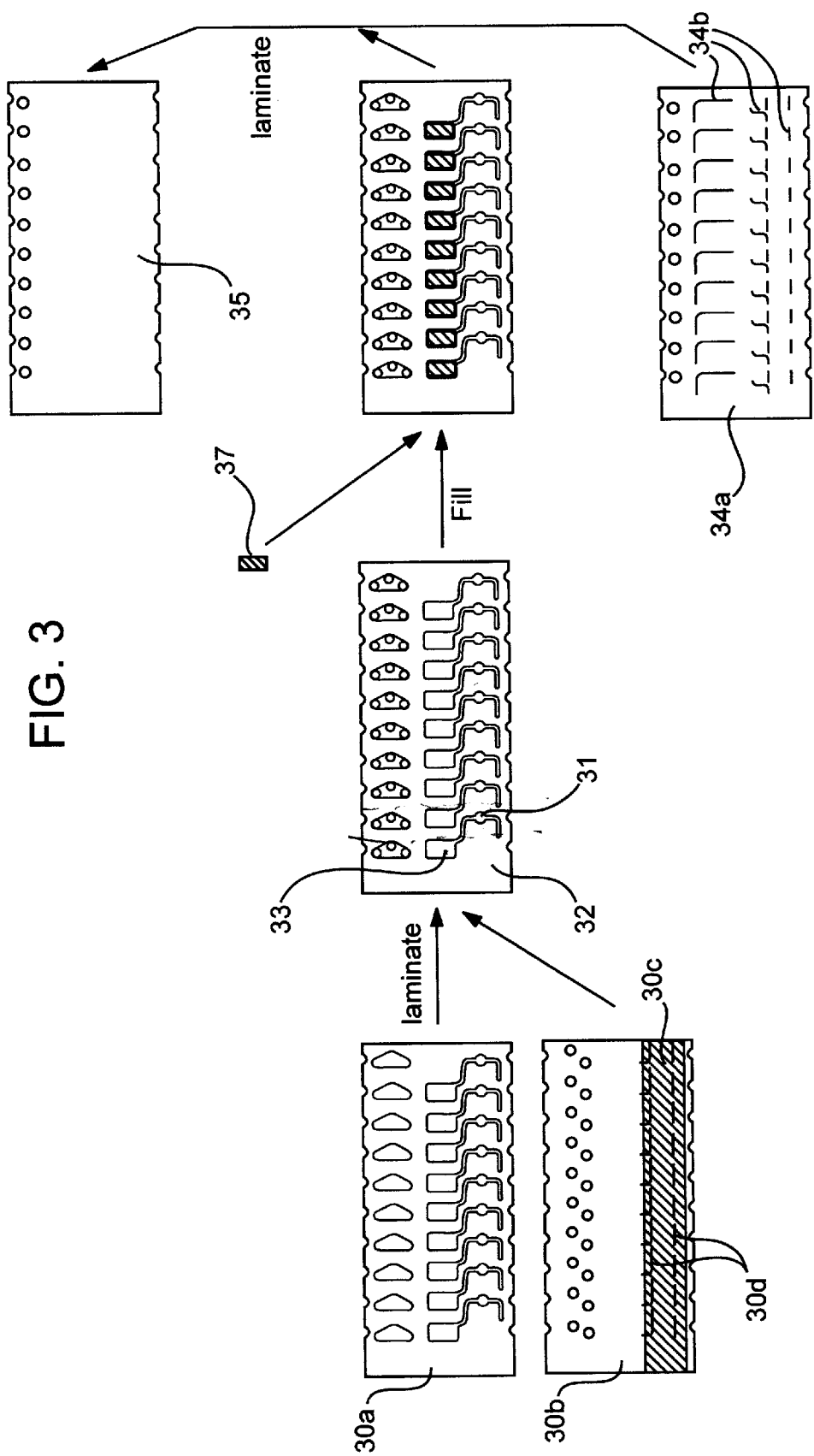

ELECTROCHEMICAL TEST STRIP CARDS THAT INCLUDE AN INTEGRAL DESSICANT

INTRODUCTION

Field of the Invention

The field of this invention is analyte determination, particularly electrochemical analyte determination and more particularly the electrochemical determination of blood analytes.

Background

Analyte detection in physiological fluids, e.g., blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of method that is employed for analyte detection is an electrochemical method. In such methods, an aqueous liquid sample is placed into a reaction zone in an electrochemical cell comprising two electrodes, i.e., a reference and working electrode, where the electrodes have an impedance which renders them suitable for amperometric measurement. The component to be analyzed is allowed to react directly with an electrode, or directly or indirectly with a redox reagent to form an oxidizable (or reducible) substance in an amount corresponding to the concentration of the component to be analyzed, i.e., analyte. The quantity of the oxidizable (or reducible) substance present is then estimated electrochemically and related to the amount of analyte present in the initial sample.

A problem faced by manufacturers and users of these types of electrochemical test strips is reagent degradation due to water exposure. For example, when the reagent composition of such strips is exposed to normal environmental humidity, the response of the test strip can change dramatically and therefore confound the results obtained with the strip.

As such, there is continued interest in the identification of new electrochemical strip configurations in which the reagent composition of the strip is protected from contact with environmental humidity. Of particular interest would be the development of a card from which a plurality of test strips could be singulated, where the reagent composition in each card is protected from water mediated degradation.

Relevant Literature

Patent documents of interest include: U.S. Pat. Nos. 5,708,247; 5,942,102; 5,951,836; 5,972,199; 5,989,917; 5,997,817; 6,151,110; 6,125,292; WO 97/18465; WO 97/27483 and EP 871 033.

SUMMARY OF THE INVENTION

Electrochemical test strip cards that can be singulated to produce electrochemical test strips are provided. The electrochemical test cards are made up of two or more electrochemical test strip precursors, where each precursor is characterized by the presence of a dry reagent housing reaction chamber bounded by opposing electrodes. In gaseous communication with each reaction chamber of the card is an integrated desiccant. Also provided are methods of using the subject electrochemical test strips cards, as well as kits that include the same. The subject test strips and cards find use in the detection/concentration determination of a number of different analytes, including glucose.

BRIEF DESCRIPTION OF THE FIGURES

FIG. 1 provides a schematic for the assembly of a first embodiment of the subject test strip cards.

FIG. 2 provides a schematic for the assembly of a second embodiment of the subject test strip cards.

FIG. 3 provides a schematic for the assembly of a third embodiment of the subject test strip cards.

FIG. 4a provides an exploded view of a test strip card according to the subject invention, while FIG. 4b provides an exploded view of a test strip that is singulated from the card shown in FIG. 4a.

FIG. 6a provides an exploded view of a test strip card according to the subject invention, while FIG. 6b provides an exploded view of a test strip that is singulated from the card shown in FIG. 6a.

FIG. 8a provides an exploded view of a test strip card according to the subject invention, while FIG. 8b provides an exploded view of a test strip that is singulated from the card shown in FIG. 8a.

FIG. 9a provides an exploded view of a test strip card according to the subject invention, while FIG. 9b provides an exploded view of a test strip that is singulated from the card shown in FIG. 9a.

FIG. 11a provides an exploded view of another test strip card according to the subject invention, while FIG. 11b provides an exploded view of a test strip that is singulated from the card shown in FIG. 11a.

DESCRIPTION OF THE SPECIFIC EMBODIMENTS

Figure 4A:
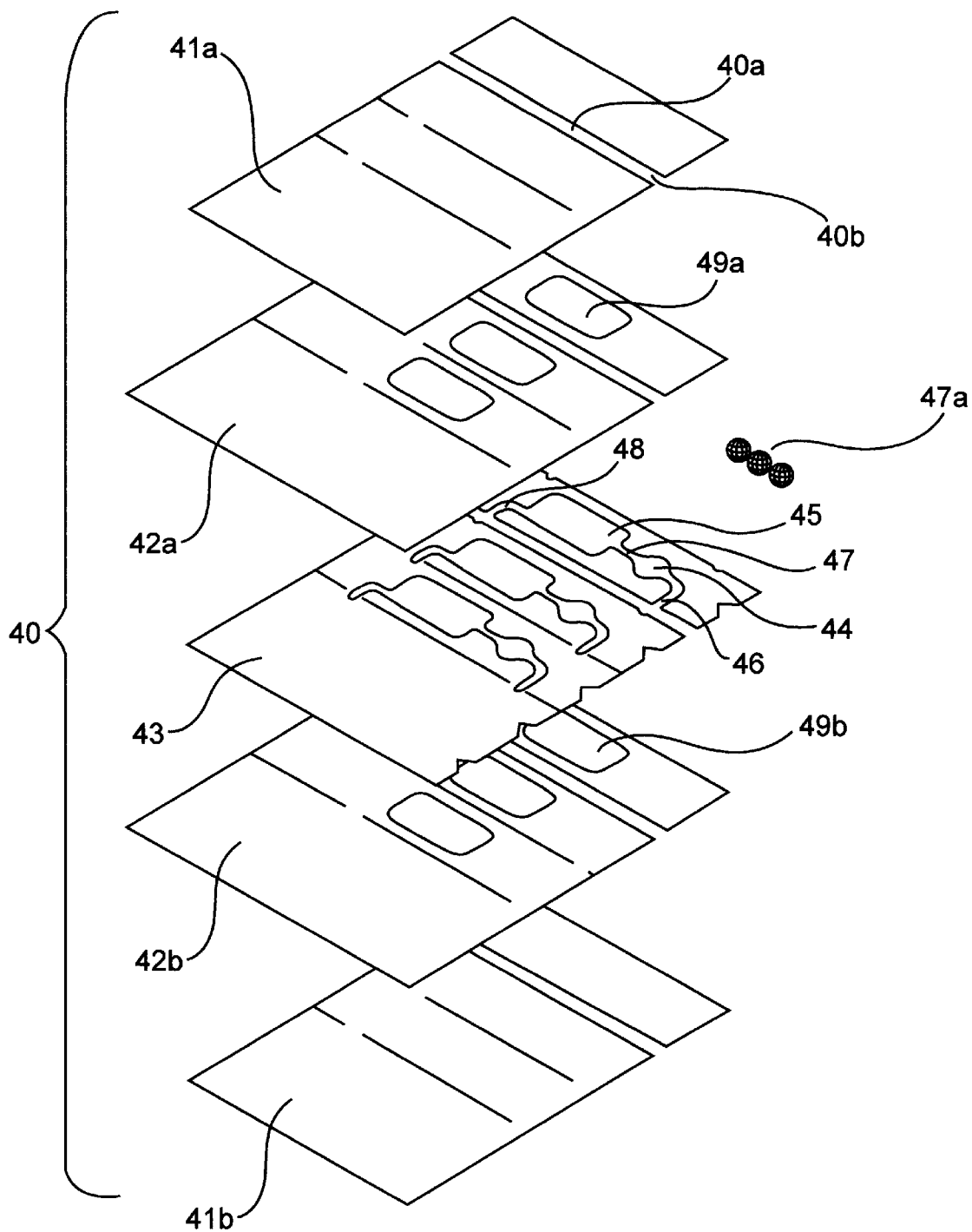

Electrochemical test strip cards that can be singulated to produce electrochemical test strips are provided. The electrochemical test cards are made up of two or more electrochemical test strip precursors, where each precursor is characterized by the presence of a dry reagent housing reaction chamber bounded by opposing electrodes. In gaseous communication with each reaction chamber of the card is an integrated desiccant. Also provided are methods of using the subject electrochemical test strips cards, as well as kits that include the same. The subject test strips and cards find use in the detection/concentration determination of a number of different analytes, including glucose.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Electrochemical Test Cards

As summarized above, the subject invention provides electrochemical test strip cards that can be singulated into electrochemical test strips. More specifically, the electrochemical test strip cards can be cut into two or more, i.e., a plurality of electrochemical test strips. Generally, the cards can be singulated or cut into from about 2 to 100, usually from about 5 to 50 and more usually from about 10 to 30 individual test strips.

As such, the test strip cards are characterized in that they include a plurality of adjacent test strip precursors, where by plurality is meant at least 2, where the number of precursors in a given card generally ranges from about 2 to 100, usually from about 5 to 50 and more usually from about 10 to 30. The dimensions of the subject cards may vary, but generally the cards have a length ranging from about 2 cm to 50 cm, usually from about 3 cm to 30 cm and more usually from about 6 cm to 20 cm and a width ranging from about 0.5 cm to 10 cm, usually from about 1 cm to 8 cm and more usually from about 2 cm to 5 cm. Thus, the test strips that can be cut from the cards generally have a length that ranges from about 0.5 cm to 10 cm, usually from about 1 cm to 8 cm and more usually from about 2 cm to 5 cm and a width that ranges from about 0.1 cm to 2.5 cm, usually from about 0.2 cm to 1.5 cm and more usually from about 0.5 cm to 1 cm.

Each precursor of the card is characterized by including at least a reaction chamber which is bounded by opposing electrodes and houses a dry reagent composition. These features of the subject precursors are described in greater detail infra in terms of the test strips that can be produced from the subject cards.

A feature of the subject invention is that an integrated desiccant for each reaction chamber is present in the subject cards. By integrated is meant that the desiccant is a component or integral feature of the card, e.g., it is a component that is incorporated into the card, a component present in one or more of the materials making up the card, e.g., a laminated covering material, etc., and the like. As the cards contain a desiccant for each reaction chamber, typically they include a plurality of desiccant materials so that an individual desiccant material is present for each reaction chamber. As such, the number of individual desiccant materials present in the cards generally ranges from about 2 to 100, usually from about 5 to 10 and more usually from about 10 to 30—one for each reaction chamber present on the card.

A variety of different types of desiccant materials may be employed, where representative desiccant materials include solid materials, e.g., beads and strips or blocks of desiccant material, etc. Each desiccant material should have a capacity of at least about 0.5 mg water per test, usually at least about 1 mg water per test and more usually at least about 1.5 mg water per test. The capacity of the desiccant materials employed in the subject cards typically ranges from 0.5 mg water per test to 10 mg water per test, usually from about 0.75 mg water per test to 5 mg water per test and more usually from about 1.0 mg water per test to 3 mg water per test. Representative materials that may be employed as desiccants include, but are not limited to: mol sieve, silica gel, $CaSO_4$, CaO and the like. Incorporated into the desiccant material may be an indicator that provides a detectable single, e.g., color change, that can be used to determine the remaining capacity of the desiccant, e.g., to determine whether or not a desiccant has reached capacity with respect to the amount of water that it can sequester. Indicator compounds of interest include, but are not limited to: $CoCl_2$ and the like.

The cards are further characterized in that, prior to singulation into individual strips, each reaction chamber of each precursor is in gaseous communication with a desiccant material present on the card. By gaseous communication is meant that at least water vapor present in the reaction chamber is freely able to move to the desiccant and be sequestered thereby.

In many embodiments, the desiccant material is generally present in, i.e., housed in, a desiccant chamber which is part of the card, and in many embodiments incorporated into each strip. The desiccant chambers must be of sufficient volume to house the desiccant materials, where the volume of the desiccant chambers generally ranges from about 0.0015 cc to 0.15 cc, usually from about 0.010 cc to 0.10 cc and more usually from about 0.015 cc to 0.08 cc. The configuration of the chamber may vary considerably and depends primarily on the dimensions of the material which is housed in the desiccant chamber.

Generally, a channel or tube connects the reaction chamber of each precursor to a desiccant chamber so that the requisite gaseous communication between the desiccant and the reaction chamber is established. The tube or channel often has a smallest dimension ranging from about 0.002 cm to 0.05 cm, usually from about 0.005 cm to 0.05 cm and may have a length that ranges from about 0 cm to 3 cm, usually from about 0.02 cm to 1.5 cm and more usually from about 0.15 cm to 5 cm.

The configuration of each desiccant chamber with respect to each reaction chamber with which it is in gaseous communication may vary. In certain embodiments, the desiccant chamber is in gaseous communication with a reaction chamber that is present on the same precursor, such that when the card is singulated, the resultant test strip has a reaction chamber that is still in gaseous communication with a desiccant material in a desiccant chamber. In alternative embodiments, the desiccant chamber is in gaseous communication with a reaction chamber that is present on an adjacent precursor, e.g., either the right or left precursor to it, such that when the card is singulated, the resultant test strip has a reaction chamber that is no longer in gaseous communication with a desiccant material.

In certain embodiments, the card is configured such that singulation results in the production of an electrochemical test strip that has fluid entry and exit channels leading into and out of the reaction chamber which provide for fluid communication between the reaction chamber and the external environment of the test strip, where no such communication existed prior to singulation. In other words, the card is configured so that when a test strip is cut from an end of the card, the cutting or singulation process results in the production of fluid ingress and egress channels between the reaction chamber and the external environment of the strip, so that fluid sample can be introduced into the reaction chamber and gas can leave the reaction chamber.

The subject test strip cards are typically present in a moisture vapor barrier material which provides for a moisture vapor impermeable barrier between the card and the external environment. The barrier material may be laminated onto the card to provide for a tight seal. Any convenient moisture vapor impermeable material may be employed, where representative materials include, but are not limited to: polyethylene, polypropylene, polystyrene, polyethylene terepthalate, rubber, polymers of fluorinated and/or chlorinated ethylene monomers, copolymers of fluorinated and/or chlorinated ethylene monomers, polymethylmethacrylate, films coated with silicon oxide and the like. In certain embodiments the cards further include calibration information; identification information, etc., which may be present on the card in the form of a scannable bar code, or other information storage means.

The design of the cards may be varied to provide for a number of different electrical contact configurations in test strips that are ultimately singulated from the cards. Representative alternative contact configurations are provided in FIGS. 1 to 3, described in greater detail infra.

Figure 4B:
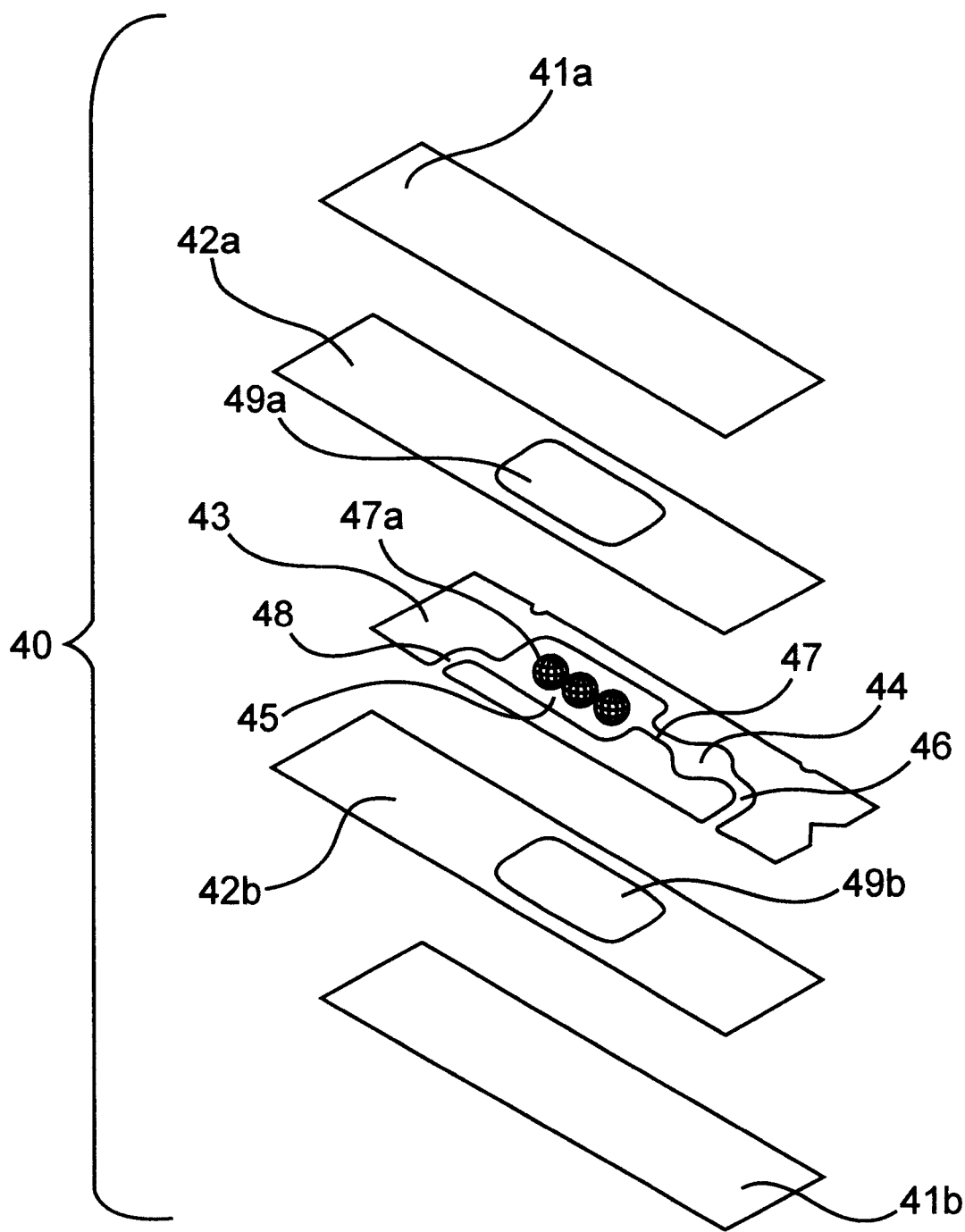
Figure 6A:
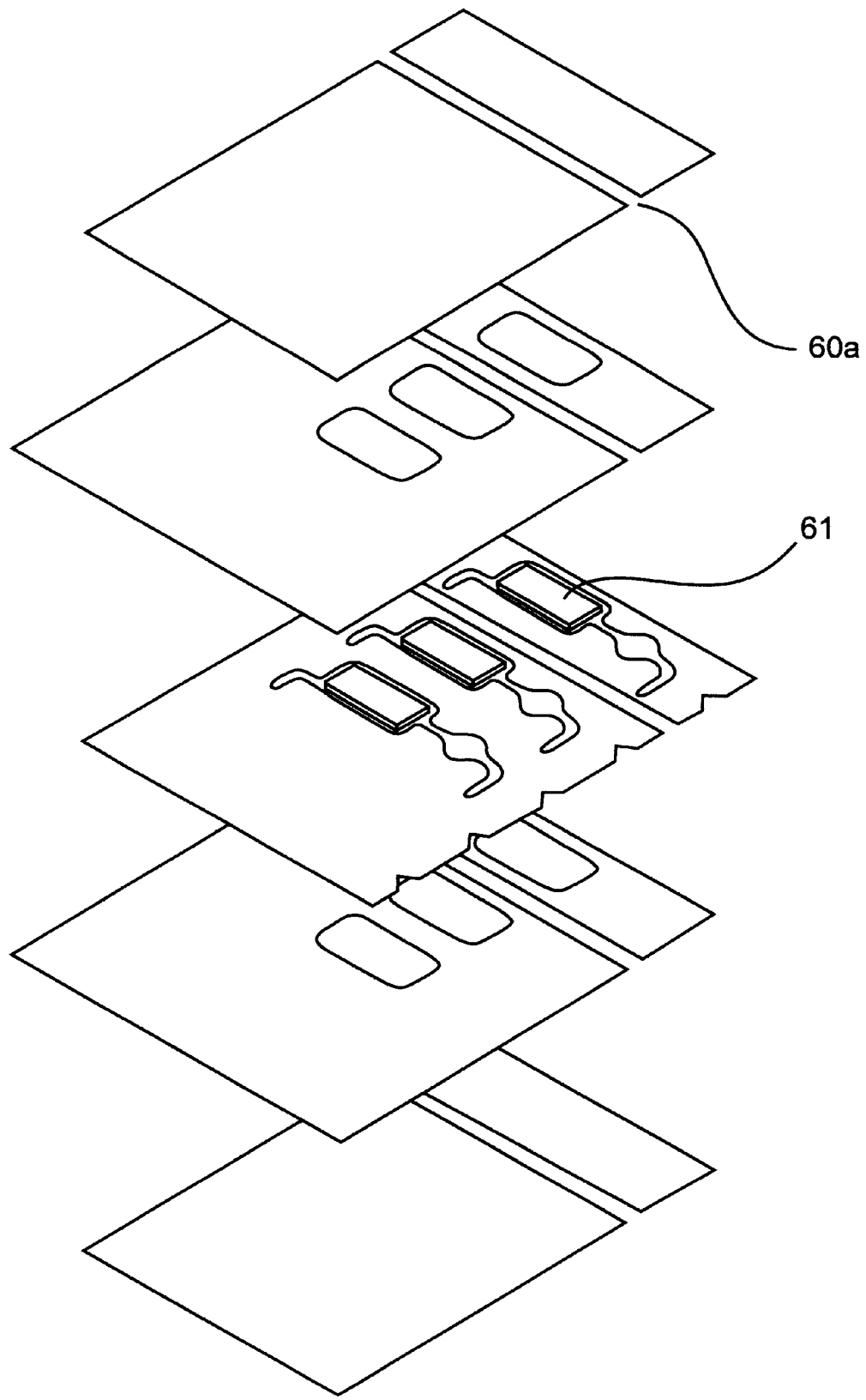
Figure 6B:
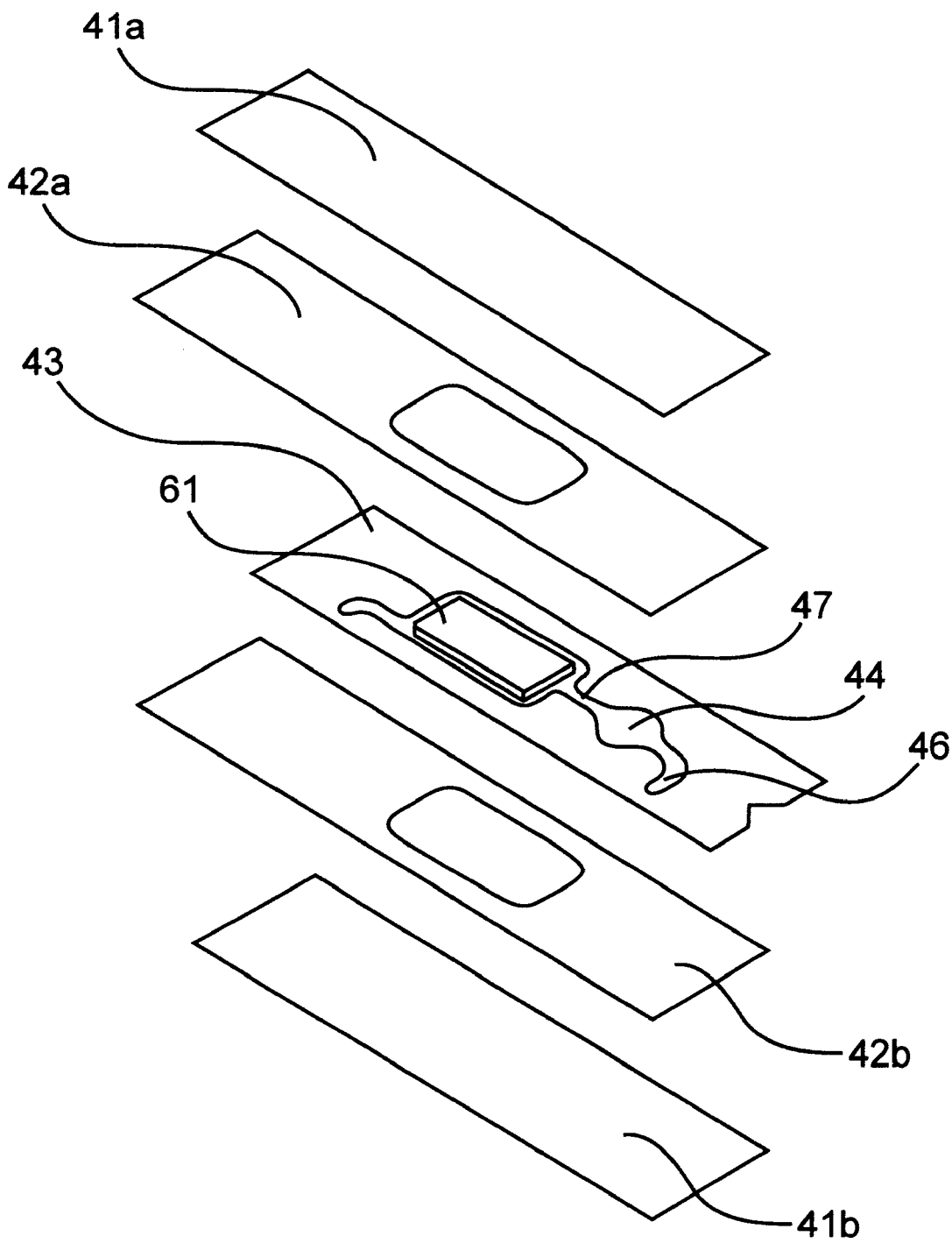
Figure 8A:
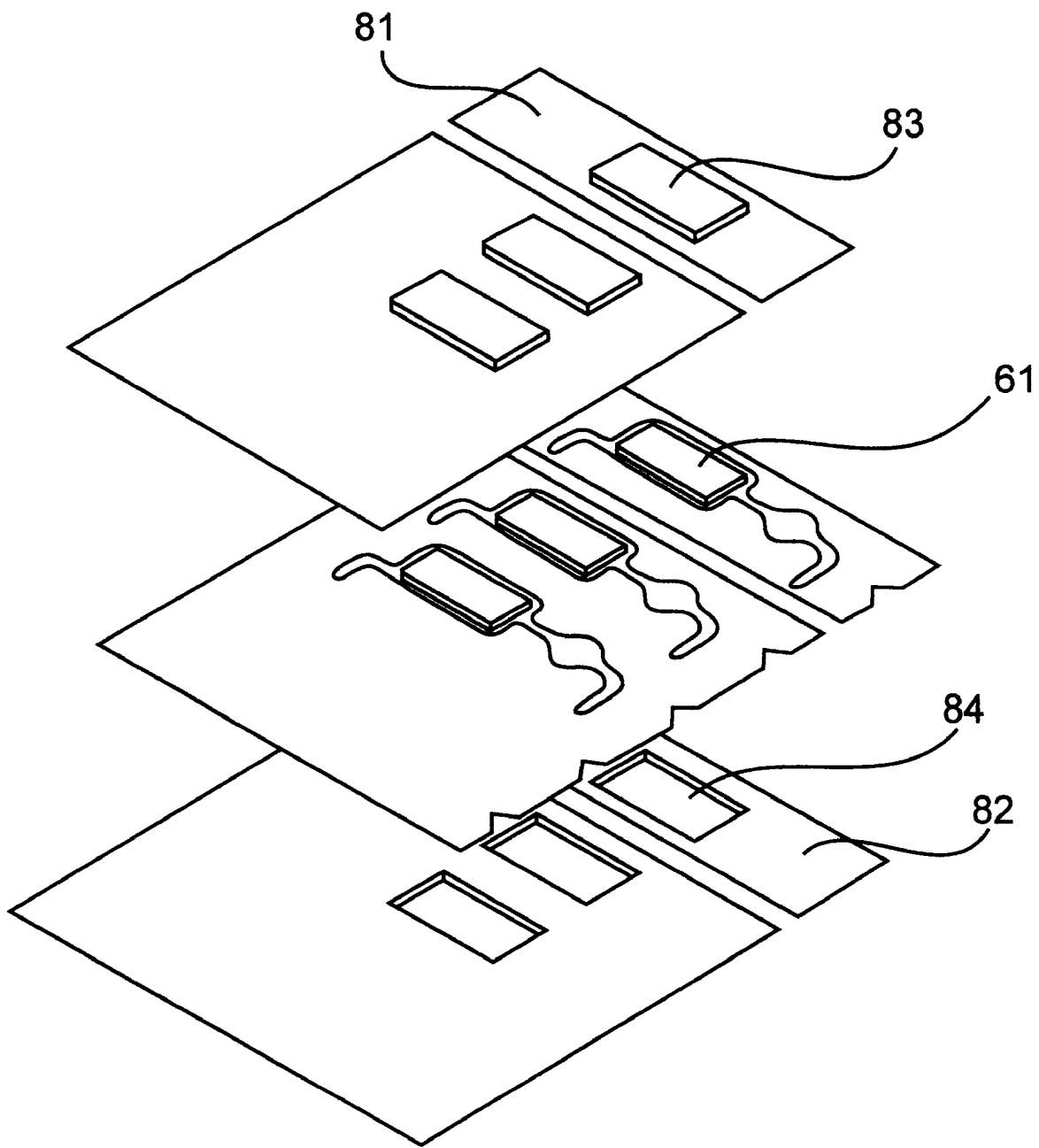
Figure 9A:
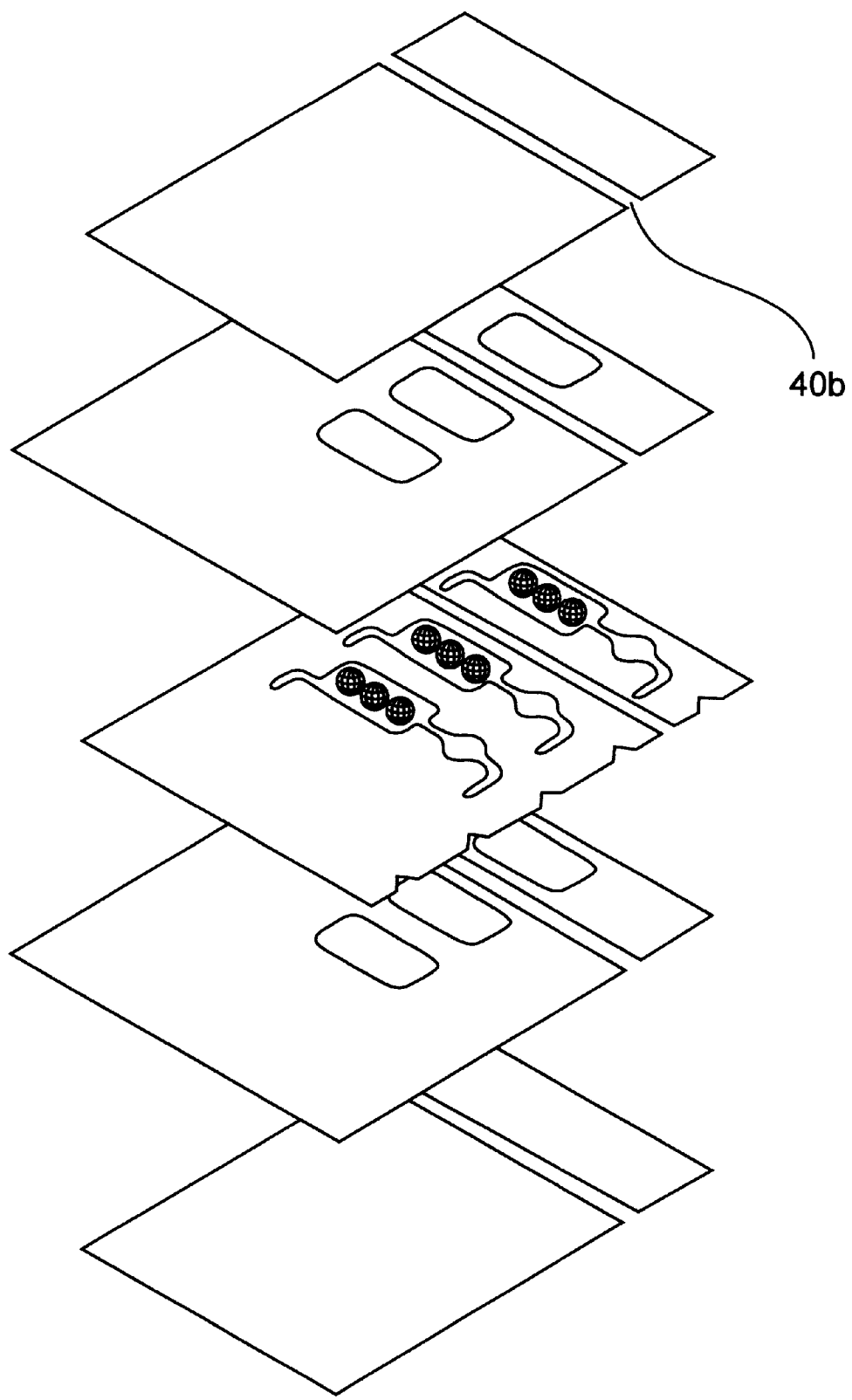

Representative test strip card configurations are now further described in terms of the figures. FIG. 4a provides an exploded view of a test strip card according to one embodiment of the subject invention, while FIG. 4b provides an exploded view of a test strip cut from the card shown in FIG. 4a. In FIG. 4a, test strip 40 is a multi-layer structure made up of top and bottom layers 41a & 41b (e.g., 3M 425, which is a lamination of 0.0028" Al foil and 0.0018" acrylic PSA), top and bottom electrode layers 42a & 42b (e.g., 0.005 clear PET, Au coat (bottom) & 0.005" clear PET, Pd coat top side, respectively), and middle spacer layer 43 (e.g., 0.003" PET, 0.001 acrylic PSA both sides). Spacer layer 43 has a pattern that provides for a reaction chamber 44, a desiccant chamber 45, fluid ingress channel 46, a channel 47 connecting the reaction chamber to the desiccant chamber, and a venting channel, 48, attached to the desiccant chamber. Desiccant 47a (e.g., 2.5 mg 4A mol seive beads) is located in the desiccant chamber. Also present are cutouts 49a & 49b in the electrode layers that allow for clearance of desiccant materials thicker than the combined thickness of 42a, 42b and 43 upon assembly of the card. These cutouts also create a stop junction at the edge of the desiccant chamber so that only a defined amount of fluid can enter the reaction chamber and channels. In this configuration of the card, singulation of the card into an individual test strip opens the fluid ingress channel such that fluid communication is established between the reaction chamber of the strip and both the external environment and the desiccant chamber. In addition, the card is configured such that singulation results in a strip in which the desiccant chamber and ultimately the fluid channels and reaction chamber are vented to the external environment, so that fluid ingression can proceed without being impeded by air pressure build-up. The test strip card of FIG. 4a has a precut 40a that provides guidance for the final cut 40b employed to singulate the cards into strips. FIG. 6a provides an exploded view of a modification of the card of FIG. 4a, where a desiccant block or tape 61 (e.g., 60% 4A mole sieve; 1–3% glycol in PETG; approx 0.2×0.15×0.025") is present in the desiccant chamber 45. Also shown is a representative singulation cut 60a. FIG. 6b shows the details of a singulated strip. In FIGS. 6a and 6b, the fluid ingression channel 46 and the vent 48 have been shortened for the purposes of the experiment described in example II. FIG. 8a provides an exploded view of a modified version of the strip shown in FIG. 6a. In FIG. 8a, the top and electrode layers have been combined into single layers 81 and 82, where single layers 81 and 82 have stamped regions 83 and 84 to accommodate desiccant block 61. FIG. 9a provides an exploded view of a modification of the strip of FIG. 4a, where channel 46 and vent 48 have been shortened according to example III. Yet another embodiment of the subject cards can be seen in FIG. 3. In FIG. 3, the design shown in FIG. 4a has been modified so that the reaction chamber 31 of each precursor is in gaseous communication with a desiccant chamber 33 present on the precursor adjacent to it. As can be seen from the figure, in this configuration singulation of the card into an individual test strip opens the fluid ingress and egress channels such that fluid communication is established between the reaction chamber of the strip and the external environment. In addition, the card is configured such that singulation results in a strip in which the reaction chamber is no longer in gaseous communication with the desiccant chamber.

Electrochemical Test Strips

As indicated above, the electrochemical test strip cards of the subject invention can be singulated or cut into individual electrochemical test strips. The subject electrochemical test strips include two opposing metal electrodes separated by a thin spacer layer, where these components define a reaction chamber, i.e., area or zone, in which is located a redox reagent system.

As indicated above, the working and reference electrodes are generally configured in the form of elongated rectangular strips. Typically, the length of the electrodes ranges from about 1.9 to 4.5 cm, usually from about 2.0 to 2.8 cm. The width of the electrodes ranges from about 0.38 to 0.76 cm, usually from about 0.51 to 0.67 cm. The reference electrodes typically have a thickness ranging from about 10 to 100 nm and usually from about 10 to 20 nm.

The working and reference electrodes are further characterized in that at least the surface of the electrodes that faces the reaction area in the strip is a metal, where metals of interest include palladium, gold, platinum, silver, iridium, carbon, doped tin oxide, stainless steel and the like. In many embodiments, the metal is gold or palladium. While in principle the entire electrode may be made of the metal, each of the electrodes is generally made up of an inert support material on the surface of which is present a thin layer of the metal component of the electrode. In these more common embodiments, the thickness of the inert backing material typically ranges from about 51 to 356 $\mu$m, usually from about 102 to 153 $\mu$m while the thickness of the metal layer typically ranges from about 10 to 100 nm and usually from about 10 to 40 nm, e.g. a sputtered metal layer. Any convenient inert backing material may be employed in the subject electrodes, where typically the material is a rigid material that is capable of providing structural support to the electrode and, in turn, the electrochemical test strip as a whole. Suitable materials that may be employed as the backing substrate include plastics, e.g. PET, PETG, polyimide, polycarbonate, polystyrene, silicon, ceramic, glass, and the like.

A feature of the electrochemical test strips produced from the subject cards is that the working and reference electrodes as described above face each other and are separated by only a short distance, such that the distance between the working and reference electrode in the reaction zone or area of the electrochemical test strip is extremely small. This minimal spacing of the working and reference electrodes in the subject test strips is a result of the presence of a thin spacer layer positioned or sandwiched between the working and reference electrodes. The thickness of this spacer layer generally should be less than or equal to 500 $\mu$m, and usually ranges from about 102 to 153 $\mu$m. The spacer layer is cut so as to provide a reaction zone or area with at least an inlet port into the reaction zone, and generally an outlet port out of the reaction zone as well, i.e., the ingress and egress channels described above. The spacer layer may have a circular reaction area cut with side inlet and outlet vents or ports, or other configurations, e.g. square, triangular, rectangular, irregular shaped reaction areas, etc. The spacer layer may be fabricated from any convenient material, where representative suitable materials include PET, PETG, polyimide, polycarbonate, and the like, where the surfaces of the spacer layer may be treated so as to be adhesive with respect to their respective electrodes and thereby maintain the structure of the electrochemical test strip. Of particular interest is the use of a die-cut double-sided adhesive strip as the spacer layer.

The electrochemical test strips produced from the subject cards include a reaction chamber, zone or area that is defined by the working electrode, the reference electrode and the spacer layer, where these elements are described above. Specifically, the working and reference electrodes define the top and bottom of the reaction area, while the spacer layer defines the walls of the reaction area. The volume of the reaction area is at least about 0.1 μL, usually at least about 1 μL and more usually at least about 1.5 μL, where the volume may be as large as 10 μL or larger. As mentioned above, the reaction area generally includes at least an inlet port, and in many embodiments also includes an outlet port. The cross-sectional area of the inlet and outlet ports may vary as long as it is sufficiently large to provide an effective entrance or exit of fluid from the reaction area, but generally ranges from about $9 \times 10^{-4}$ to $5 \times 10^{-3}$ cm$^2$, usually from about $1.3 \times 10^{-3}$ to $2.5 \times 10^{-3}$ cm$^2$.

Present in the reaction area is a redox reagent system, which reagent system provides for the species that is measured by the electrode and therefore is used to derive the concentration of analyte in a physiological sample. The redox reagent system present in the reaction area typically includes at least an enzyme(s) and a mediator. In many embodiments, the enzyme member(s) of the redox reagent system is an enzyme or plurality of enzymes that work in concert to oxidize the analyte of interest. In other words, the enzyme component of the redox reagent system is made up of a single analyte oxidizing enzyme or a collection of two or more enzymes that work in concert to oxidize the analyte of interest. Enzymes of interest include oxidases, dehydrogenases, lipases, kinases, diphorases, quinoproteins, and the like.

The specific enzyme present in the reaction area depends on the particular analyte for which the electrochemical test strip is designed to detect, where representative enzymes include: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In many preferred embodiments where the analyte of interest is glucose, the enzyme component of the redox reagent system is a glucose oxidizing enzyme, e.g. a glucose oxidase or glucose dehydrogenase.

The second component of the redox reagent system is a mediator component, which is made up of one or more mediator agents. A variety of different mediator agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. In those embodiments where glucose in the analyte of interest and glucose oxidase or glucose dehydrogenase are the enzyme components, mediators of particular interest are ferricyanide, and the like.

Other reagents that may be present in the reaction area include buffering agents, e.g. citraconate, citrate, malic, maleic, phosphate, "Good" buffers and the like. Yet other agents that may be present include: divalent cations such as calcium chloride, and magnesium chloride; pyrroloquinoline quinone; types of surfactants such as Triton, Macol, Tetronic, Silwet, Zonyl, and Pluronic; stabilizing agents such as albumin, sucrose, trehalose, mannitol, and lactose.

The redox reagent system is generally present in dry form.

Card and Test Strip Manufacture

The subject electrochemical test strip cards may be fabricated using any convenient procedure. In many embodiments, various layers of different materials, e.g., electrode layers, spacer layers, etc., are brought together into a single card format, which is then laminated in a barrier material to produce the final product. Representative protocols for fabricating different types of cards according to the subject invention are now described in terms of the figures. However, the following description of representative card manufacture protocols is merely illustrative, and should in no way be considered limiting, as the cards may be fabricated using any convenient protocol, as mentioned above.

FIG. 1 provides a schematic representation of the fabrication of a test strip card according to one embodiment of the invention. In the process illustrated in FIG. 1, the initial starting materials are top electrode layer 1a, bottom electrode layer 1b and middle spacer layer 1c. In this example, top electrode layer 1a is a PET substrate with a sputtered gold layer on the bottom, while the bottom electrode layer 1b is a PET substrate with a sputtered palladium layer on the top. Reagents (1d) are coated onto the bottom layer. Spacer layer is a 3-layer lamination of PSA/PET/PSA (PSA=pressure sensitive adhesive; PET=polyester terepthalate) which has the precursor fluid pathways and reaction chamber present. These three layers are laminated together to produce structure 2 and a hole 3 is punched through the composite laminate structure to produce a desiccant chamber. Punching of the desiccant chamber also results in the production of a fluid stop junction downstream from the reaction chamber which serves to precisely limit the amount of fluid sample that enters the strip upon use, as described below. A desiccant material (4), e.g., block, beads, etc., is then positioned in the punched out desiccant chamber and the resulting structure is laminated or sealed between top and bottom barrier layers 5a and 5b consisting of, e.g., PSA-faced aluminum film to produce the final card 6. If the layers 5a and 5b are sufficiently malleable, the film will deform during lamination to allow for the thickness of the desiccant. If the materials can be embossed, they may be be embossed prior to lamination to form a pocket which accepts the desiccant material. At the end of card 6 is an information storage means, e.g., barcode, transmitter, etc., which provides information such as calibration information to the meter with which the card is employed. As can be seen, the configuration of the various electrode layers provides for electrical contacts in the final strips singulated from the cards.

Also shown in FIG. 1 are features cut in the various layers to allow contacts in the meter to touch the metallized surfaces of the electrode films which face the inside of the strip. Additionally, marks (1e) are shown that indicate lines cut through the metallized layer, but not the backing material, of the electrode layers, which lines form electrically isolated areas on the electrode surface. These isolation features serve two purposes: (1) an electrode is formed at the end of the flow channel which allows detection of complete fluid fill of the device, and (2) the area of the channel actually being used as the electrode is potentially limited to areas defined by the features.

An alternate card format that can be produced by the same process is illustrated in FIG. 2. In FIG. 2, the configuration of the initial top and bottom electrode layers have been modified to provide for an alternate electrical contact scheme in the electrochemical test strips singulated from the card. Analogous to the manufacture process depicted in FIG. 1, the first step in the process of FIG. 2 is to provide top electrode layer 21a, bottom electrode layer 21b and middle spacer layer 21c. Additionally, marks (21e) are shown that indicate lines cut through the metallized layer, but not the backing material, of the electrode layers, which lines form electrically isolated areas on the electrode surface. Reagent material 21d is present on the surface of bottom electrode 21b. The precursors 21a–21c are laminated to produce structure 22 and hole is punched out in structure 22 to produce a dessicant chamber 23. A desiccant material (24), e.g., block, beads, etc., is then positioned in the punched out desiccant chamber and the resulting structure is laminated or sealed between top and bottom barrier layers 25a and 25b consisting of, e.g., PSA-faced aluminum film to produce the final card 26. FIG. 3 provides a schematic illustration of a second protocol that may be employed to fabricate the subject cards. In the process illustrated in FIG. 3, an initial bottom and spacer layer, 30b & 30a, respectively, are employed. The bottom layer 30b has a metal upper surface with a reagent stripe (30c) printed thereon. The bottom electrode layer has electrode zones defined by isolation cuts 30d. Middle spacer layer 30 a is characterized by having a flow path that includes a desiccant chamber, where the desiccant chamber 33 is in communication with the reaction chamber in the adjacent strip precursor. The bottom and middle layers are first laminated together to produce structure 32, and desiccant material 37 is positioned in the desiccant chamber 33. Structure 32 is then laminated to top electrode layer 34a (which has electrode isolation cuts 34b) to produce final card 35. In the embodiment shown in FIG. 3, the electrode film serves two functions: (a) support for the metal layer and (b) as a primary moisture barrier. In this embodiment, the film is composed of a material with low moisture vapor transmission rates, such as the Aclar material available from Allied Signal. A pocket is pre-formed in the film, e.g., by stamping or thermoforming, to accept the desiccant material. The outer barrier of the film is directly adjacent to the spacer layer, so a stop junction cannot be formed by the desiccant chamber. Therefore, the desiccant chamber is positioned on the adjacent strip, such that a stop junction is produced upon singulation of the card into strips.

To produce electrochemical test strips from the cards, the cards are singulated or cut into the test strips. Any convenient cutting or separation protocol may be employed, including slitting, shearing, punching, laser singulation, etc. In certain embodiments, singulation is performed by the meter with which the strip is employed.

Methods of Use

In using the electrochemical test strips produced from the subject cards, a quantity of the physiological sample of interest is introduced into the electrochemical cell of the reaction chamber of the test strip. The physiological sample may vary, but in many embodiments is generally whole blood or a derivative or fraction thereof, where whole blood is of particular interest in many embodiments. The amount of physiological sample, e.g., blood, that is introduced into the reaction area of the test strip varies, but generally ranges from about 0.1 to 10 μL, usually from about 0.9 to 1.6 μL. The sample is introduced into the reaction area using any convenient protocol, where the sample may be injected into the reaction area, allowed to wick into the reaction area, and the like, as may be convenient.

Following application of the sample to the reaction zone, an electrochemical measurement is made using the reference and working electrodes. The electrochemical measurement that is made may vary depending on the particular nature of the assay and the device with which the electrochemical test strip is employed, e.g. depending on whether the assay is coulometric, amperometric or potentiometric. Generally, the electrochemical measure will measure charge (coulometric), current (amperometric) or potential (potentiometric), usually over a given period of time following sample introduction into the reaction area. Methods for making the above described electrochemical measurement are further described in U.S. Pat. Nos.: 4,224,125; 4,545,382; and 5,266,179; as well as WO 97/18465; WO 99/49307; the disclosures of which are herein incorporated by reference.

Following detection of the electrochemical signal generated in the reaction zone as described above, the amount of the analyte present in the sample introduced into the reaction zone is then determined by relating the electrochemical signal to the amount of analyte in the sample. In making this derivation, the measured electrochemical signal is typically compared to the signal generated from a series of previously obtained control or standard values, and determined from this comparison. In many embodiments, the electrochemical signal measurement steps and analyte concentration derivation steps, as described above, are performed automatically by a devices designed to work with the test strip to produce a value of analyte concentration in a sample applied to the test strip. A representative reading device for automatically practicing these steps, such that user need only apply sample to the reaction zone and then read the final analyte concentration result from the device, is further described in copending U.S. Pat. No. 6,193,873.

The methods may be employed to determine the concentration of a variety of different analytes, where representative analytes include glucose, cholesterol, lactate, alcohol, and the like. In many preferred embodiments, the subject methods are employed to determine the glucose concentration in a physiological sample. While in principle the subject methods may be used to determine the concentration of an analyte in a variety of different physiological samples, such as urine, tears, saliva, and the like, they are particularly suited for use in determining the concentration of an analyte in blood or blood fractions, e.g., blood derived samples, and more particularly in whole blood.

Kits

Also provided by the subject invention are kits for use in practicing the subject invention. The kits of the subject invention at least include an electrochemical test strip, as described above. The subject kits may further include a means for obtaining a physiological sample. For example, where the physiological sample is blood, the subject kits may further include a means for obtaining a blood sample, such as a lance for sticking a finger, a lance actuation means, and the like. In addition, the subject kits may include a control solution or standard, e.g., a glucose control solution that contains a standardized concentration of glucose. Finally, the kits include instructions for using the subject reagent test strip cards in the determination of an analyte concentration in a physiological sample. These instructions may be present on one or more of the packaging, a label insert, containers present in the kits, and the like. Alternatively, a means for remotely accessing such instructions, e.g., at an internet site, may be provided, where such means may take the form of a URL printed onto a substrate present in the kit, e.g., package insert, packaging etc.

The following examples are offered by way of illustration and not by way of limitation.

Experimental

EXAMPLE I

Palladium and gold coated polyester films were treated with mercapto-ethane sulfonic acid (MESA) by dipping in a 0.6 M MESA solution, followed by air drying. The palladium foil was laminated to a spacer layer with the channel shape shown in FIG. 4a. A pyrrolo-quinoline-quinone (PQQ)—glucose dehydrogenase (GDH) reagent was formulated as follows:

Solution A
  1.1 g $CaCl_2$+100 mL deionized water
Solution B
  99.5 mL (0.1 M Citracconic acid, pH 6.5, 0.02% Silwet 7600)+0.5 mL A
Solution C
  1 mg PQQ+27.5 mL B
Solution D
  1.12 g $K_4Fe(CN)_6$+5 mL B
Solution E
  3.21 mg GDH (502 U/mg)+300 µL C incubate for 30 minutes at RT in the dark add 100 µL D 1.5 µL of the reagent was applied with a pipet to the reagent zone (1f in FIG. 1), and air dried on a 50° C. hot plate. The gold coated film was applied to the top of the spacer layer, and the punched desiccant chamber was created as shown in FIG. 1. At this point, cards were finished by either inserting three 4A mol sieve beads (approx. 2 mg each) and covering with aluminum foil (3M 425), or laminating another layer of 0.005" gold-coated polyester film to cover the punched hole. The three mol sieve beads together had a total capacity of about 1.2 mg of water.

The cards were stored for 32 days either in a 75% RH, room temperature chamber, or desiccated (4A mol sieve) in at 5° C. At intervals during the study, cards were removed, strips were singulated and then developed with 42% hematocrit blood adjusted to approximately 0, 40 and 450 mg/dl glucose. A different donor's blood was employed at each time point, but the refrigerated control was included for comparison in the case of any donor-related effects (and differences in actual glucose levels). 6–9 strips were developed for each case.

Figure 5A:
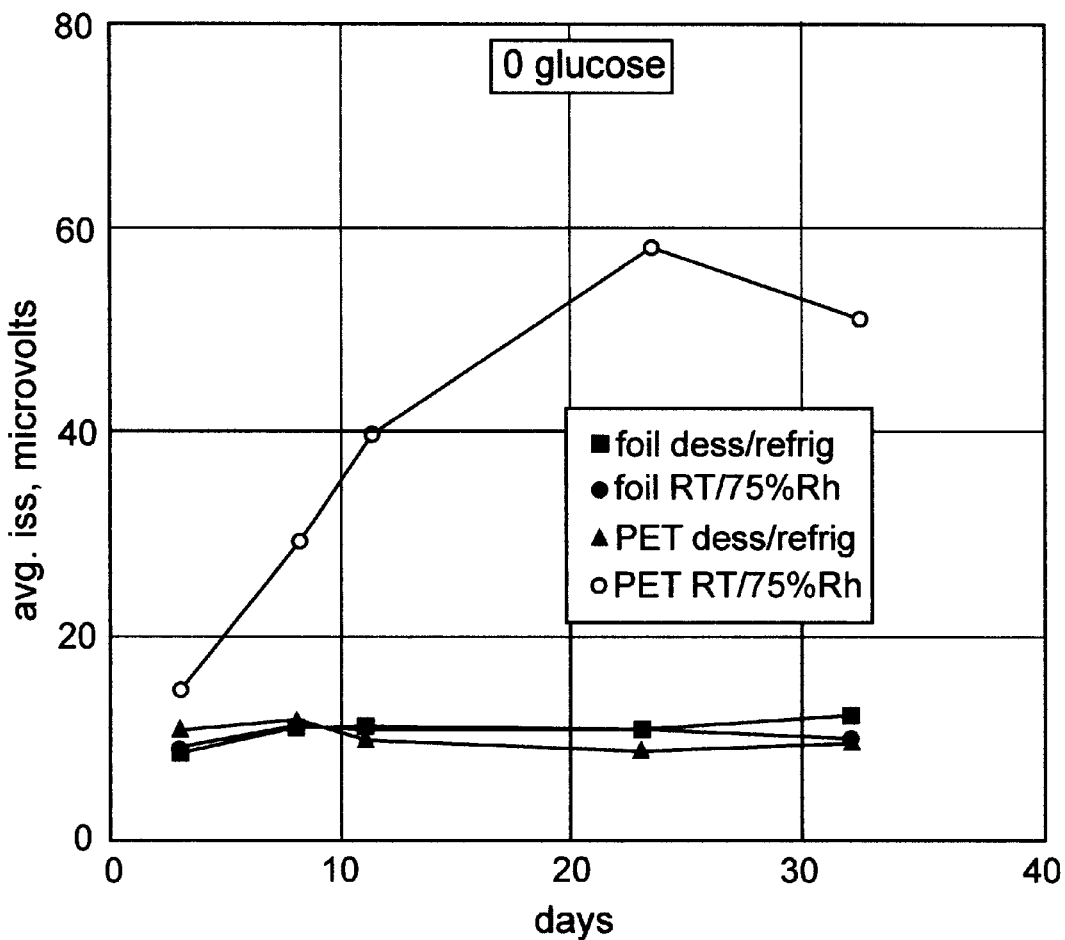
FIGS. 5a to 5c provide graphical results of the data obtained from the experiments reported in Example I.
Figure 5B:
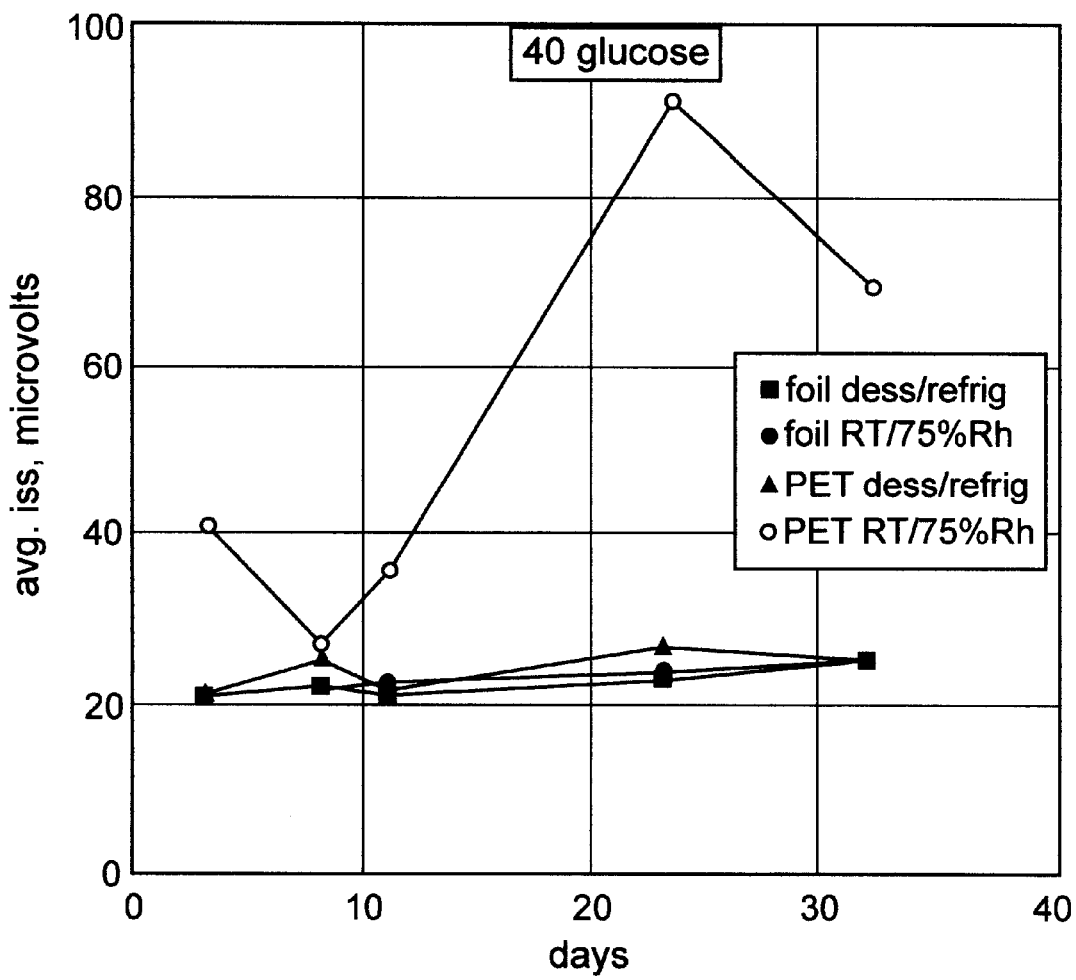
Figure 5C:
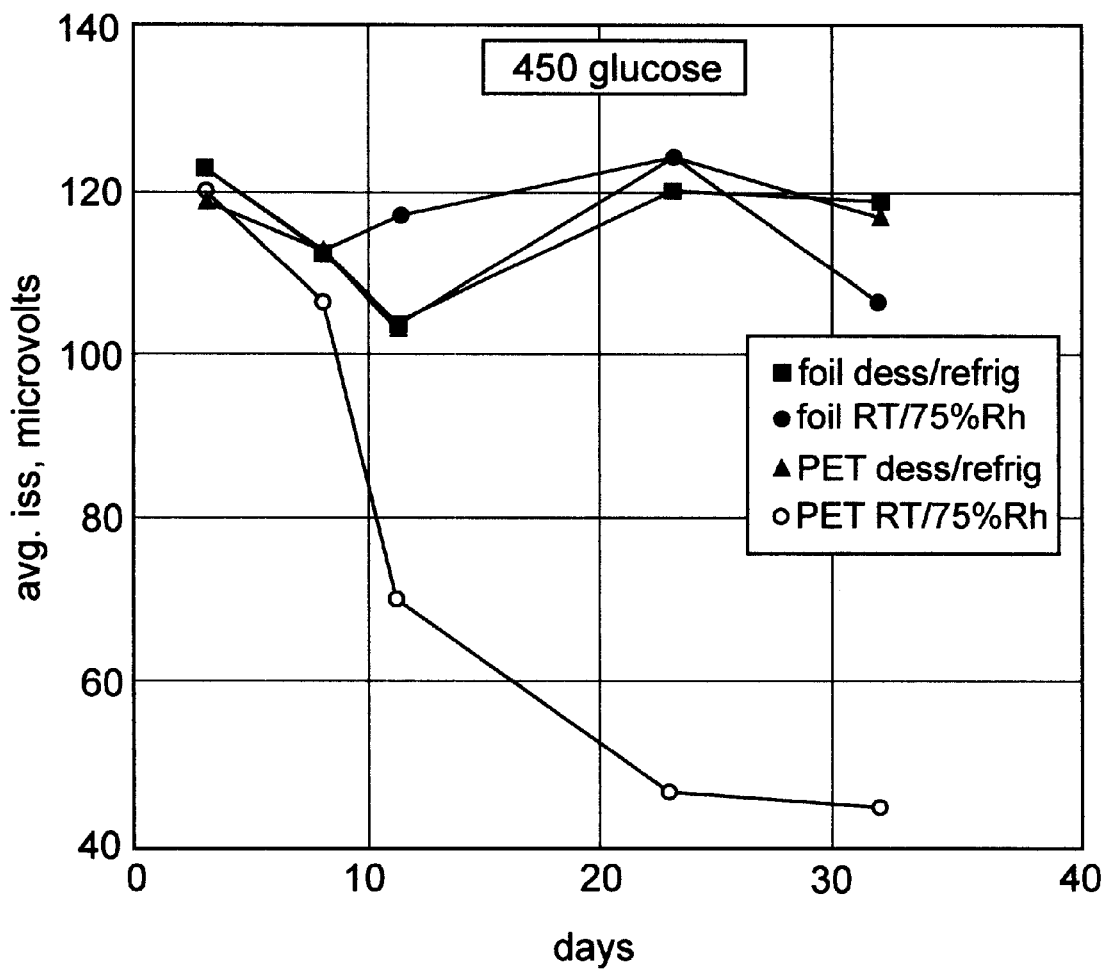

The device which read the strips applied a +50 mV potential across the electrodes to detect sample application. When a current increase signaled sample application, the potential was changed to −300 mV and held there for 5 seconds. After 5 seconds, the potential was changed to +300 mV and held there for 9 seconds. During the +300 mV phase, the decaying current vs time curve was projected mathematically to infinity; this infinity current value was termed $i_{SS}$. $I_{SS}$ is approximately proportional to glucose concentration. FIGS. 5a, 5b and 5c show the averaged $i_{SS}$ values for the two cases and the refrigerated control. At zero glucose, a small (about 10 microvolt) background current is seen initially for all cases. This current remains essentially unchanged for all cases except the PET case exposed to high humidity, where it increased dramatically as the study progressed, indicating a build-up of ferrocyanide. At 40 mg/dl glucose, the effect was essentially the same. At 450 glucose, where the glucose-related current was much higher, the increase in current due to ferrocyanide production on exposure was not as noticeable as a decrease in $i_{SS}$ due to enzyme degradation. Again, this degradation effect occurred only in the PET high humidity case. Clearly, the foil-faced internally desiccated strips were far more stable when challenged with this high humidity environment for up to 32 days.

EXAMPLE II

In this example, cards similar to the aluminum-faced cards in example I were prepared, with one exception (see FIGS. 6a and 6b). The sample entrance and vent channels were shortened so that when strips were singulated, the channel system was still completely sealed inside the strip, and the tips of the sample and vent channels ended 0.030" from the edge of the strip (this merely involved shortening the channels by 0.060"). This configuration was intended to simulate a card configuration in which cuts are made between strips at time of manufacture to minimize the force required for singulation, as outlined above. Samples were prepared both as complete, uncut cards, and as singulated strips. Each configuration was also prepared with and without desiccant in the desiccant chamber.

Figure 7:
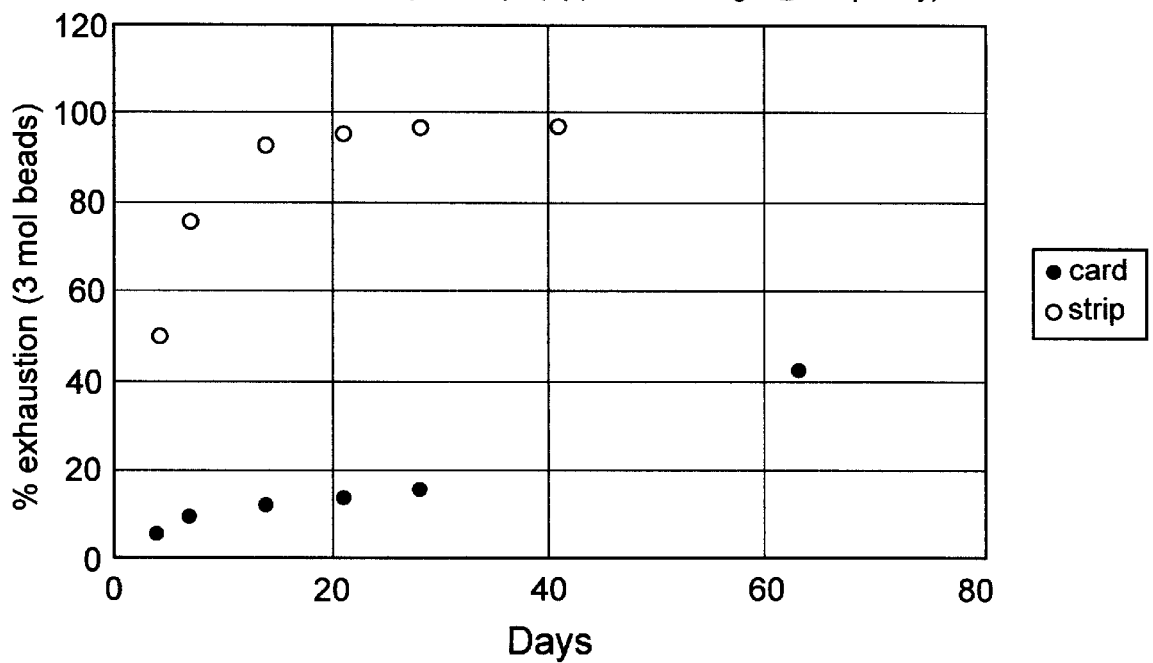
FIG. 7 provides graphical results of the data obtained from the experiments reported in Example II.

To investigate the effect of the cuts on moisture ingression, and to correlate the previously observed card stability with moisture inside the package, a moisture uptake study was conducted as follows: 40 individual strips were prepared for each singulated strip case, and 2 20-strip cards were prepared for the card cases. All four cases were placed in the 75% RH, room temperature chamber. Over the next 63 days, all materials in each case were weighed to assess moisture uptake. To compute the amount of moisture passing through the strip or card package, the weight gain of the non-desiccant case was subtracted from that of its corresponding desiccant-containing configuration. Based on the observation that each of the 3 beads per strip weighed about 2 mg and could absorb about 20% of its weight in moisture, the percent exhaustion of the desiccant was calculated at each time point. FIG. 7 shows the results.

The complete card configuration had slightly more than 40% exhaustion of the desiccant in 63 days. In example I, the good reagent stability seen up to 32 days with complete cards, in retrospect, corresponds to about 18% exhaustion of the desiccant. Because mol sieve maintains very low relative humidity even at significant degrees of exhaustion, one would good reagent stability to be found up to 40% exhaustion as well.

The singulated strip configuration, on the other hand, reached 50% exhaustion in about 5 days; significantly faster than the complete card. The singulation cut opens up routes which speed up moisture ingression. Thus with this foil-faced configuration, the meter would probably have to make the entire cut between strips. Also, the life of the end strip (and possibly the next one or so) might be less than interior strips.

EXAMPLE III

Figure 8B:
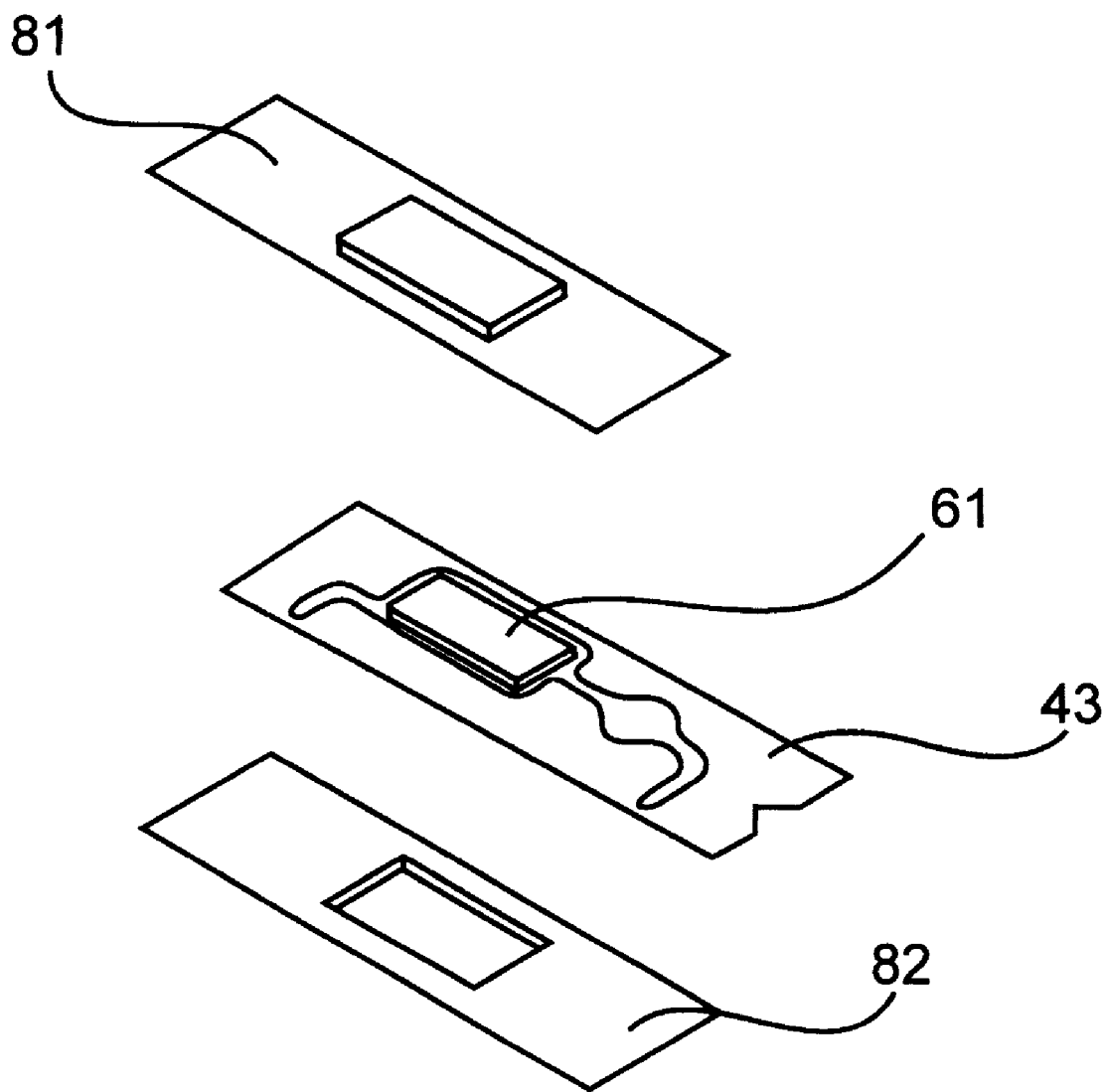
Figure 9B:
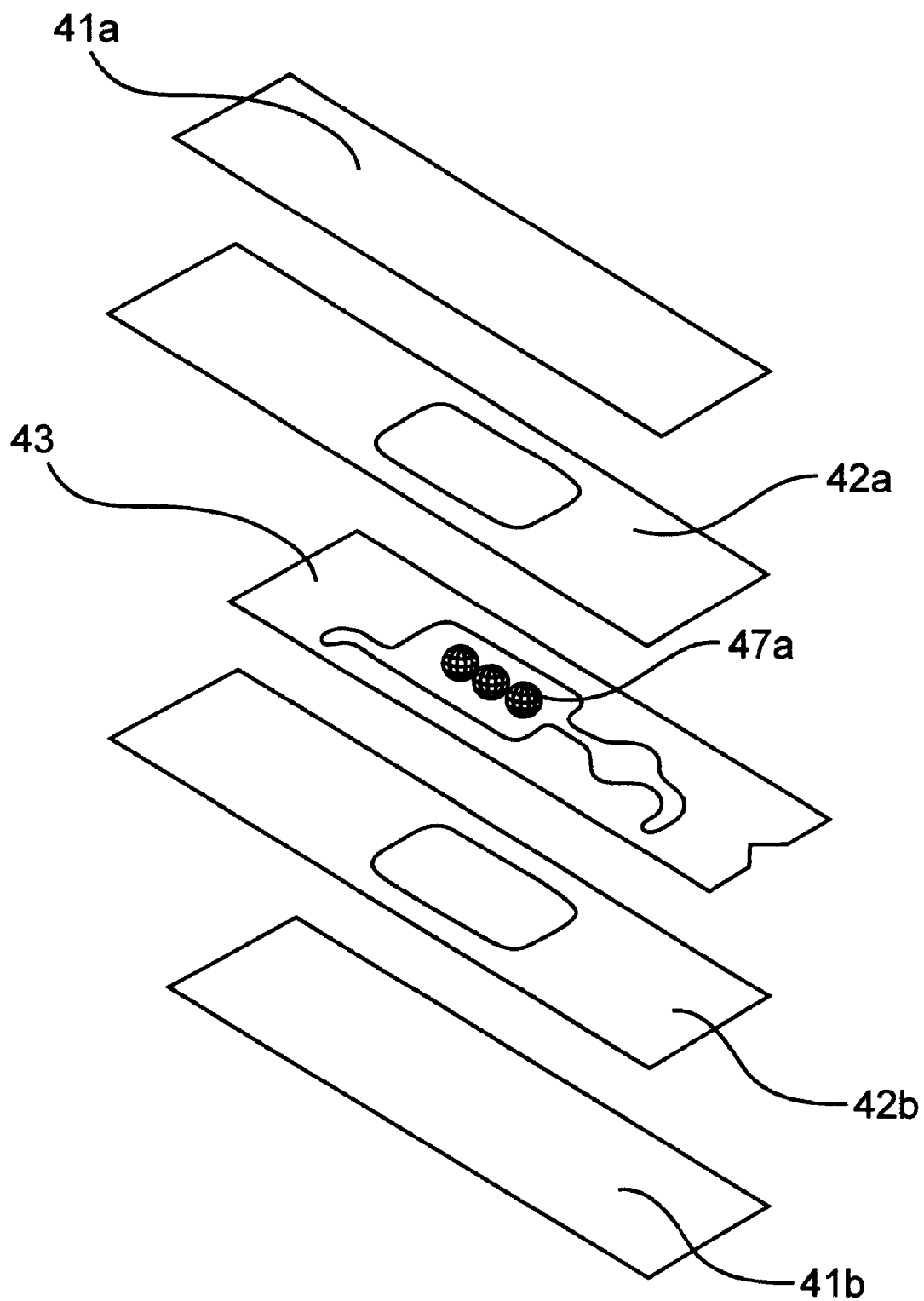
Figure 10A:
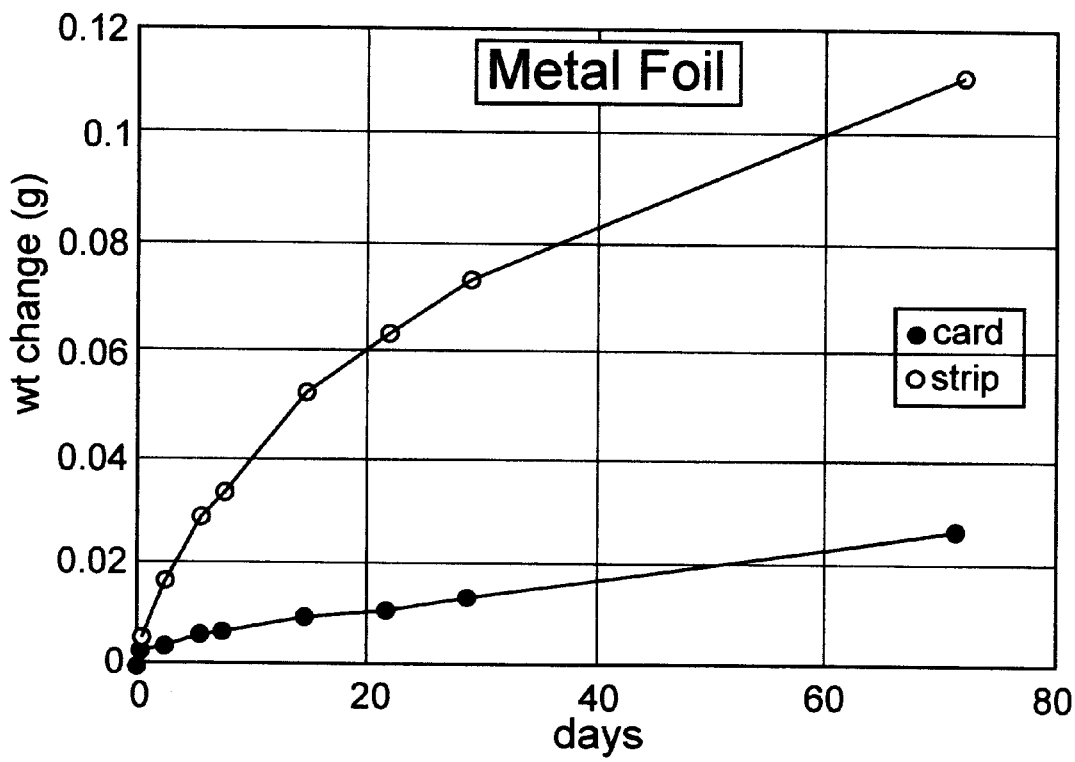
FIGS. 10a to 10b provide graphical results of the data obtained from the experiments reported in Example III.
Figure 10B:
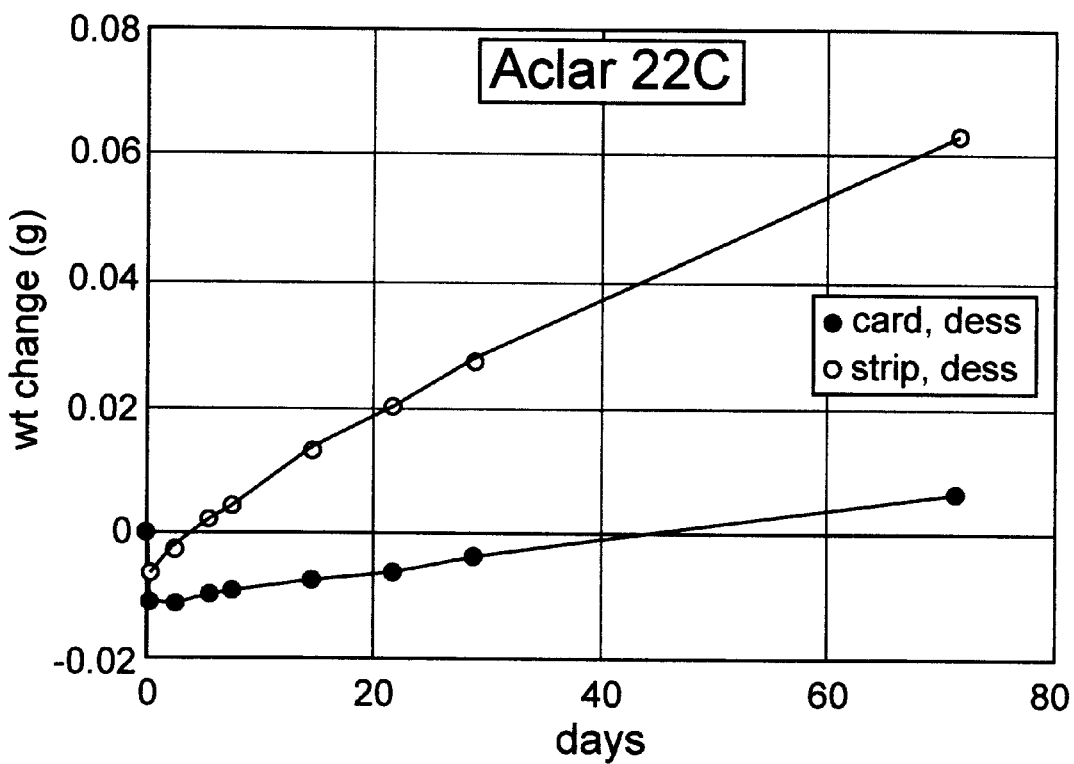
Figure 11A:
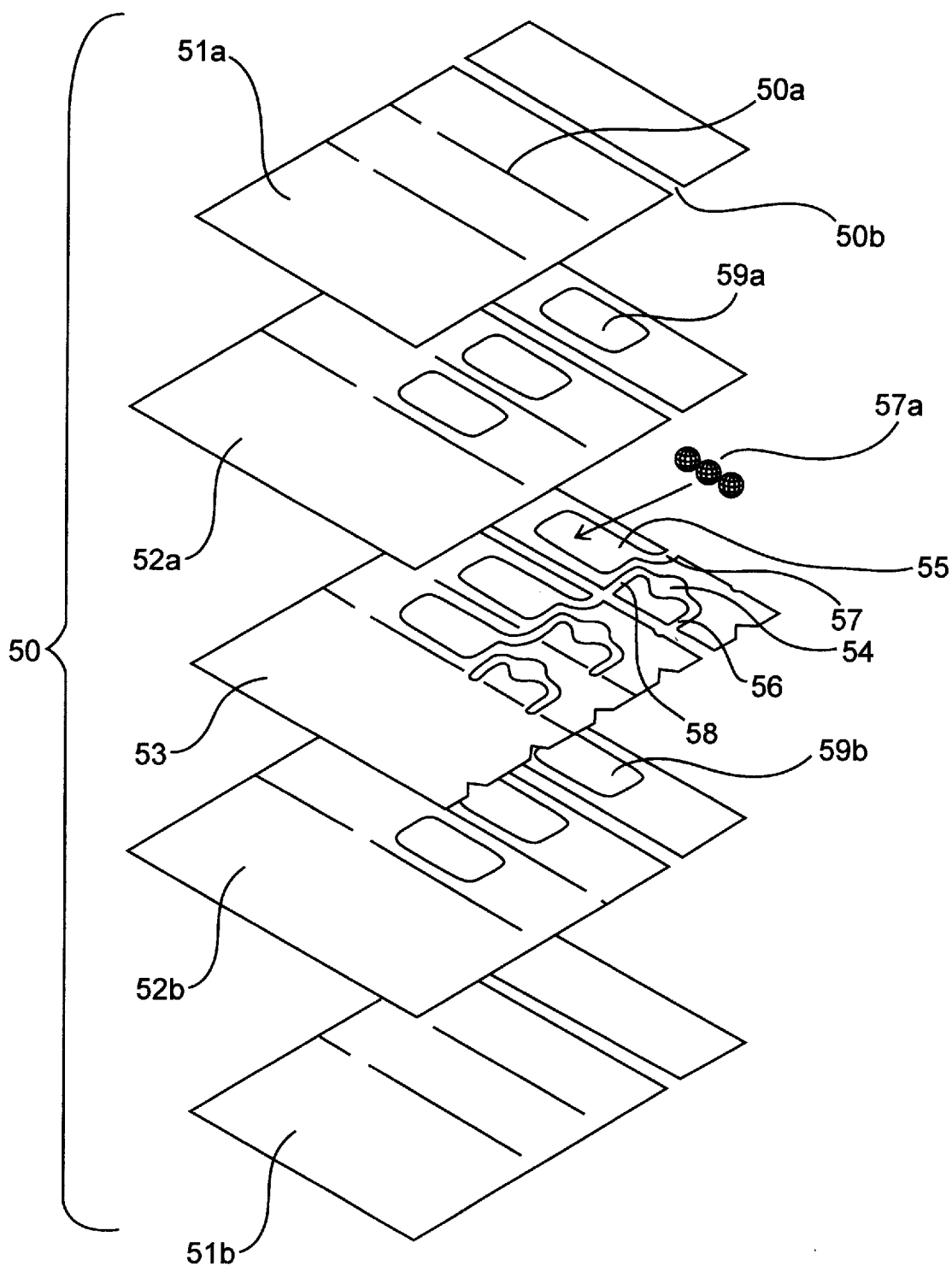
Figure 11B:
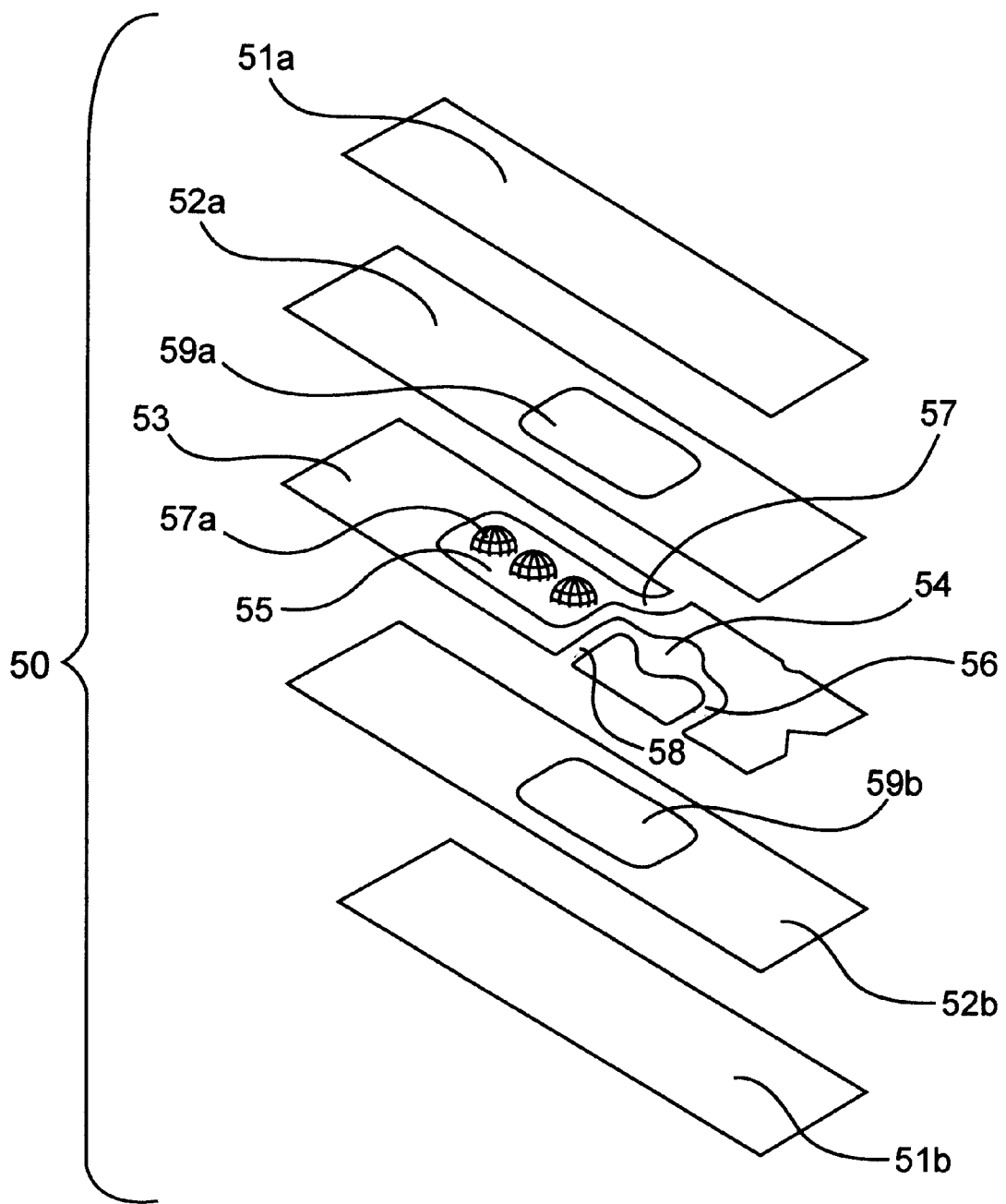

See FIGS. 8a and 8b. In this example, cards were made as in example II, except that (1) the rectangular shape of the desiccant chamber was cut into the center spacer layer, (2) metallized PET and the foil outer layers were replaced with a single layer of 0.005" Aclar 22C, (3) a 0.028" pocket was formed (by cold stamping) in one layer of the Aclar to conform to the shape of the desiccant chamber and (4) a 13 mg piece mg piece of 0.025" desiccant tape consisting of about 60% mol sieve powder and 1–3% glycol in PETG (Capital vial) was used as desiccant. The desiccant had a total capacity of about 2.6 mg of water per strip, or about 2.3×the capacity of the 3 mol sieve beads in examples I and II. For comparison, foil faced cards were made as in I and II, but the mol sieve beads were replaced with the same amount of desiccant tape as the Aclar cards (see FIGS. 9a and 9b). Both types of cards were also made without desiccant as a control for moisture absorption by the outside of the package, and all configurations were subjected to 75% RH as cards and cut strips. 40 strips were tested per case FIGS. 10a and 10b show the results. The foil singulated strips in this example exhibited much better moisture resistance than in example II: the 50% exhaustion level was reached at about 12 days rather than in 5 days; this is approximately what would have been predicted from the increased desiccant capacity.

The Aclar 22C data shows an anomalous exhaustion decrease between day 0 and day 1; this is undoubtedly a weighing error at day 0. After allowing for this offset (all exhaustion values should be about 5–10% higher), it is clear that at 28 days, the cut strips have not gained enough moisture to exhaust the desiccant more than 35%, and that the desiccant should certainly be less than 50% exhausted at 30 days. Thus the change in materials and amount of desiccant have both contributed to achieving a design where even if pre-singulation cuts are made between strips, the strips should remain dry enough to last at least one month, and end strips should be just as good as center strips.

The Aclar strip used in this example is intended to be a model for moisture vapor transmission through a package similar to the intended device.

The above results and discussion demonstrate that improvements in electrochemical test strip technology are provided by the subject invention. Specifically, the subject invention provides for storage stable multi-strip cards or tapes that can be singulated as needed by the end user, which will provide for less use of packaging materials and more efficient and cost effective manufacture protocols, among other advantages. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An electrochemical test strip card, said card comprising;
    at least two electrochemical test strip precursors configured to be singulated from said card, wherein each of said precursors comprises:
        (a) a reaction chamber bounded by opposing electrodes and comprising a reagent composition; and
        (b) an integrated desiccant;
        wherein prior to singulation of said card and during use of an electrochemical test strip, each reaction chamber is in gaseous communication with a desiccant of said card.

2. The electrochemical test strip card according to claim 1, wherein each electrochemical test strip precursor further comprises a desiccant chamber that houses a desiccant material.

3. The electrochemical test strip card according to claim 2, wherein said desiccant chamber is in gaseous communication with a reaction chamber on the same precursor.

4. The electrochemical test strip card according to claim 1, wherein said desiccant has a capacity of at least about 0.5 mg per test.

5. The electrochemical test strip card according to claim 1, wherein said desiccant comprises an indicator.

6. The electrochemical test strip card according to claim 1, wherein said card is configured such that singulation of a precursor from said card provides a singulated electrochemical test strip having fluid entry and exit channels into said reaction chamber of said singulated electrochemical test strip.

7. The electrochemical test strip card according to claim 1, wherein said test strip card is sealed in a fluid barrier material.

8. The electrochemical test strip card according to claim 1, wherein said reagent composition comprises a redox reagent system comprising an enzyme and a mediator.

9. An electrochemical test strip comprising:
    (a) a reaction chamber bounded by opposing electrodes and comprising a reagent composition; and
    (b) a desiccant integrated into said electrochemical test strip wherein during use of said electrochemical test strip said reaction chamber is in gaseous communication with said desiccant.

10. The electrochemical test strip according to claim 9, wherein said electrochemical test strip further comprises a desiccant chamber that houses said desiccant.

11. The electrochemical test strip according to claim 9, wherein said desiccant has a capacity of at least about 0.5 mg per test.

12. The electrochemical test strip according to claim 9, wherein said desiccant comprises an indicator.

13. The electrochemical test strip according to claim 9, wherein said reagent composition comprises a redox reagent system that includes an enzyme and a mediator.

14. A method for determining the concentration of an analyte in a physiological sample, said method comprising:
    (a) introducing said physiological sample into an electrochemical test strip comprising:
        (i) a reaction chamber bounded by opposing electrodes and comprising a reagent composition; and
        (ii) a desiccant integrated into said electrochemical test strip;
    (b) detecting an electrical signal in said reaction zone using said electrodes; and
    (c) relating said detected electrical signal to the amount of said analyte in said sample.

15. The method according to claim 14, wherein said physiological sample is whole blood or a derivative thereof.

16. The method according to claim 14, wherein said analyte is glucose.

17. The method according to claim 14, wherein said reagent composition comprises a redox reagent system comprising an enzyme and a mediator.

18. The method according to claim 14, wherein said method further comprises singulating a test strip card to produce said electrochemical test strip prior to said introducing step (a).

19. The method according to claim 14, wherein said detecting an electrical signal and said relating said detected electrical signal are performed by an automated device.

20. A method for determining the concentration of an analyte in a physiological sample, said method comprising:
    (a) singulating an electrochemical test strip card to produce an electrochemical test strip, said card comprising at least two electrochemical test strip precursors, wherein each of said precursors comprises:

(i) a reaction chamber bounded by opposing electrodes and comprising a reagent composition; and (ii) an integrated desiccant; prior to singulation of said card, each reaction chamber is in gaseous communication with a desiccant of said card;

(b) following said singulation, introducing said physiological sample into said singulated electrochemical test strip;

(c) detecting an electrical signal in said reaction zone using said electrodes; and (d) relating said detected electrical signal to the amount of said analyte in said sample.

21. A kit for use in determining the concentration of an analyte in a physiological sample, said kit comprising:

(a) an electrochemical test strip card comprising at least two electrochemical test strip precursors configured to be singulated from said test strip card, wherein each of said precursors comprises:

(i) a reaction chamber bounded by opposing electrodes and comprising a reagent composition; and (ii) an integrated desiccant;

wherein prior to after singulation of said card each reaction chamber is in gaseous communication with said integrated dessicant; and (b) at least one of:

(i) a means for obtaining said physiological sample; and (ii) an analyte standard.

22. The kit according to claim 21, wherein said kit further comprises a meter.

23. A system for use in determining the concentration of an analyte in a physiological sample, said system comprising:

(a) an electrochemical test strip comprising:

(i) a reaction chamber bounded by opposing electrodes and comprising a reagent composition; and (ii) a desiccant integrated into said electrochemical test strip wherein during use of said electrochemical test strip said reaction chamber is in gaseous communication with said desiccant; and (b) a meter.

24. An electrochemical test strip card, said card comprising;

at least two electrochemical test strip precursors configured to be singulated from said card, wherein each of said precursors comprises:

(a) a reaction chamber bounded by opposing electrodes and comprising a reagent composition; and (b) a desiccant chamber housing a desiccant material;

wherein prior to singulation of said card, each reaction chamber is in gaseous communication with a desiccant of an adjacent percursor.

25. The electrochemical test strip card according to claim 24, wherein when said electrochemical test strips are singulated, each comprises a reaction chamber that is not in gaseous communication with a desiccant chamber.

26. The electrochemical test strip according to claim 25, wherein said strip is present in a meter.

27. An electrochemical test strip comprising:

(a) a reaction chamber bounded by opposing electrodes and comprising a reagent composition; and (b) a desiccant chamber housing a desiccant, wherein said desiccant chamber is not in gaseous communication with said reaction chamber.

* * * * *